United States Patent
Wang et al.

(10) Patent No.: US 9,861,342 B2
(45) Date of Patent: Jan. 9, 2018

(54) ADJUNCTIVE ULTRASOUND PROCESSING AND DISPLAY FOR BREAST CANCER SCREENING

(71) Applicant: U-Systems, Inc., Sunnyvale, CA (US)

(72) Inventors: Shih-Ping Wang, Los Altos, CA (US);
Donald Chin, Palo Alto, CA (US);
Fangyi Rao, San Jose, CA (US); Nico Karssemeijer, Sunnyvale, CA (US)

(73) Assignee: U-Systems, Inc., Sunnyvale, CA (US)

( * ) Notice: Subject to any disclaimer, the term of this patent is extended or adjusted under 35 U.S.C. 154(b) by 636 days.

(21) Appl. No.: 13/863,259

(22) Filed: Apr. 15, 2013

(65) Prior Publication Data

US 2013/0289405 A1 Oct. 31, 2013

Related U.S. Application Data

(63) Continuation of application No. 12/546,339, filed on Aug. 24, 2009, now abandoned, which is a
(Continued)

(51) Int. Cl.
*A61B 8/08* (2006.01)
*A61B 6/00* (2006.01)
*A61B 8/00* (2006.01)

(52) U.S. Cl.
CPC ............ *A61B 8/5215* (2013.01); *A61B 6/463* (2013.01); *A61B 6/502* (2013.01); *A61B 6/5247* (2013.01);
(Continued)

(58) Field of Classification Search
None
See application file for complete search history.

(56) References Cited

U.S. PATENT DOCUMENTS 3,556,081 A 1/1971 Jones
3,765,403 A 10/1973 Brenden
(Continued)

FOREIGN PATENT DOCUMENTS

DE 19753571 A1 6/1999
DE 19902521 A1 7/2000
(Continued)

OTHER PUBLICATIONS

Bassett, L., "Automated and Hand-Held Breast US: Effect on Patient Management", Radiology 165, pp. 103-108 (1987).
(Continued)

*Primary Examiner* — Patricia Park
(74) *Attorney, Agent, or Firm* — McCoy Russell LLP

(57) ABSTRACT

An adjunctive ultrasound mammography system and associated methods use an adjunctive ultrasound display configured for quick, intuitive, interactive viewing of volumetric ultrasound scans, displayed near a conventional x-ray mammogram display. Preferred navigations among a thick-slice image array, a selected enlarged thick-slice image, and planar ultrasound views are described, including a mode in which the planar ultrasound views are updated in real time as a cursor is moved across an active thick-slice image. In one example the thick-slice images are inverted prior to display, with non-breast areas of the image preferably segmented out and reset to dark. The inverted thick-slice images are of more familiar significance to radiologists as they are more like conventional x-ray mammograms and allow benign features to be more easily dismissed as compared to non-inverted thick-slice images. Preferred embodiments emphasize larger mass lesions and that compensate for mass lesions that straddle thick-slice region borders.

9 Claims, 21 Drawing Sheets

Related U.S. Application Data continuation of application No. 10/305,936, filed on Nov. 27, 2002, now Pat. No. 7,597,663, which is a continuation-in-part of application No. 10/160,836, filed on May 31, 2002, now Pat. No. 7,556,602, which is a continuation-in-part of application No. PCT/US01/43237, filed on Nov. 19, 2001.

(60) Provisional application No. 60/252,946, filed on Nov. 24, 2000, provisional application No. 60/326,715, filed on Oct. 3, 2001, provisional application No. 60/415,385, filed on Oct. 1, 2002.

(52) U.S. Cl.
CPC ............ *A61B 6/563* (2013.01); *A61B 8/0825* (2013.01); *A61B 8/406* (2013.01); *A61B 8/4281* (2013.01); *A61B 8/463* (2013.01); *A61B 8/464* (2013.01); *A61B 8/465* (2013.01); *A61B 8/466* (2013.01); *A61B 8/467* (2013.01); *A61B 8/5238* (2013.01); *A61B 8/565* (2013.01); *A61B 6/5241* (2013.01); *A61B 8/4405* (2013.01)

(56) References Cited

U.S. PATENT DOCUMENTS

| | | |
|---|---|---|
| 4,167,180 A | 9/1979 | Kossoff |
| 4,282,880 A | 8/1981 | Gardineer et al. |
| 4,298,009 A | 11/1981 | Mezrich et al. |
| 4,478,084 A | 10/1984 | Hassler et al. |
| 4,485,819 A | 12/1984 | Igl |
| 4,722,345 A | 2/1988 | Ueno et al. |
| 4,729,019 A | 3/1988 | Rouvrais |
| 4,796,632 A | 1/1989 | Boyd et al. |
| 4,930,143 A | 5/1990 | Lundgren et al. |
| 5,078,142 A | 1/1992 | Siczek et al. |
| 5,079,698 A | 1/1992 | Grenier et al. |
| 5,099,848 A | 3/1992 | Parker et al. |
| 5,133,020 A | 7/1992 | Giger et al. |
| 5,346,057 A | 9/1994 | Fisher et al. |
| 5,379,769 A | 1/1995 | Ito et al. |
| 5,396,890 A | 3/1995 | Weng |
| 5,413,211 A | 5/1995 | Faulkner |
| 5,433,202 A | 7/1995 | Mitchell et al. |
| 5,479,927 A | 1/1996 | Shmulewitz |
| 5,488,952 A | 2/1996 | Schoolman |
| 5,491,627 A | 2/1996 | Zhang et al. |
| 5,503,152 A | 4/1996 | Oakley et al. |
| 5,511,026 A | 4/1996 | Cleveland et al. |
| 5,603,326 A | 2/1997 | Richter |
| 5,640,956 A | 6/1997 | Getzinger et al. |
| 5,660,185 A | 8/1997 | Shmulewitz et al. |
| 5,662,109 A | 9/1997 | Hutson |
| 5,664,573 A | 9/1997 | Shmulewitz |
| 5,671,294 A | 9/1997 | Rogers et al. |
| 5,673,332 A | 9/1997 | Nishikawa et al. |
| 5,709,206 A | 1/1998 | Teboul |
| 5,729,620 A | 3/1998 | Wang |
| 5,734,384 A | 3/1998 | Yanof et al. |
| 5,776,062 A | 7/1998 | Nields |
| 5,779,641 A | 7/1998 | Hatfield et al. |
| 5,790,690 A | 8/1998 | Doi et al. |
| 5,803,082 A | 9/1998 | Stapleton et al. |
| 5,815,591 A | 9/1998 | Roehrig et al. |
| 5,820,552 A | 10/1998 | Crosby et al. |
| 5,828,774 A | 10/1998 | Wang |
| 5,833,627 A | 11/1998 | Shmulewitz et al. |
| 5,840,032 A | 11/1998 | Hatfield et al. |
| 5,851,180 A | 12/1998 | Crosby et al. |
| 5,852,475 A * | 12/1998 | Gupta .................. G06T 5/20 348/606 |
| 5,865,750 A | 2/1999 | Hatfield et al. |
| 5,899,863 A | 5/1999 | Hatfield et al. |
| 5,904,653 A | 5/1999 | Hatfield et al. |
| 5,917,929 A | 6/1999 | Marshall et al. |
| 5,919,139 A | 7/1999 | Lin |
| 5,934,288 A | 8/1999 | Avila et al. |
| 5,935,071 A | 8/1999 | Schneider et al. |
| 5,938,613 A | 8/1999 | Shmulewitz |
| 5,954,650 A | 9/1999 | Saito et al. |
| 5,964,707 A | 10/1999 | Fenster et al. |
| 5,983,123 A | 11/1999 | Shmulewitz |
| 5,984,870 A | 11/1999 | Giger et al. |
| 5,997,477 A | 12/1999 | Sehgal |
| 6,027,457 A | 2/2000 | Shmulewitz et al. |
| 6,029,797 A | 2/2000 | Olsson |
| 6,035,056 A | 3/2000 | Karssemeijer |
| 6,059,727 A | 5/2000 | Fowlkes et al. |
| 6,068,597 A | 5/2000 | Lin |
| 6,075,879 A | 6/2000 | Roehrig et al. |
| 6,091,841 A | 7/2000 | Rogers et al. |
| 6,102,861 A | 8/2000 | Avila et al. |
| 6,102,866 A | 8/2000 | Nields et al. |
| 6,117,080 A | 9/2000 | Schwartz |
| 6,123,733 A | 9/2000 | Dalton |
| 6,125,194 A * | 9/2000 | Yeh .................. G06F 19/321 382/132 |
| 6,155,978 A | 12/2000 | Cline et al. |
| 6,157,697 A | 12/2000 | Mertelmeier et al. |
| 6,178,224 B1 | 1/2001 | Policher et al. |
| 6,181,769 B1 | 1/2001 | Hoheisel et al. |
| 6,190,334 B1 | 2/2001 | Lasky et al. |
| 6,198,838 B1 | 3/2001 | Roehrig et al. |
| 6,237,750 B1 | 5/2001 | Damkjaer et al. |
| 6,246,782 B1 | 6/2001 | Shapiro et al. |
| 6,254,538 B1 | 7/2001 | Downey et al. |
| 6,263,092 B1 | 7/2001 | Roehrig et al. |
| 6,266,435 B1 | 7/2001 | Wang |
| 6,269,565 B1 | 8/2001 | Inbar et al. |
| 6,277,074 B1 | 8/2001 | Chaturvedi et al. |
| 6,278,793 B1 | 8/2001 | Gur et al. |
| 6,282,305 B1 | 8/2001 | Huo et al. |
| 6,301,378 B1 | 10/2001 | Karssemeijer et al. |
| 6,311,419 B1 | 11/2001 | Inbar |
| 6,317,617 B1 | 11/2001 | Gilhuijs et al. |
| 6,332,034 B1 * | 12/2001 | Makram-Ebeid ........ G06K 9/34 382/128 |
| 6,334,847 B1 | 1/2002 | Fenster et al. |
| 6,377,838 B1 | 4/2002 | Iwanczyk et al. |
| 6,385,474 B1 | 5/2002 | Rather et al. |
| 6,389,305 B1 * | 5/2002 | Deban .................. A61B 5/015 600/408 |
| 6,396,940 B1 | 5/2002 | Carrott et al. |
| 6,413,219 B1 | 7/2002 | Avila et al. |
| 6,421,454 B1 * | 7/2002 | Burke .................. A61B 8/4416 382/131 |
| 6,450,962 B1 | 9/2002 | Brandl et al. |
| 6,459,925 B1 | 10/2002 | Nields et al. |
| 6,461,298 B1 | 10/2002 | Fenster et al. |
| 6,524,246 B1 | 2/2003 | Kelly et al. |
| 6,530,885 B1 | 3/2003 | Entrenkin et al. |
| 6,574,499 B1 | 6/2003 | Dines et al. |
| 6,628,815 B2 | 9/2003 | Wang |
| 6,630,937 B2 | 10/2003 | Kallergi et al. |
| 6,636,584 B2 | 10/2003 | Johnson et al. |
| 6,682,484 B1 | 1/2004 | Entrekin et al. |
| 6,801,645 B1 * | 10/2004 | Collins ................ G06K 9/4609 378/37 |
| 6,876,879 B2 | 4/2005 | Dines et al. |
| 6,909,792 B1 | 6/2005 | Carrott et al. |
| 7,103,205 B2 | 9/2006 | Wang et al. |
| 7,556,602 B2 | 7/2009 | Zhang et al. |
| 2002/0173722 A1 | 11/2002 | Hoctor et al. |
| 2003/0000810 A1 | 1/2003 | Hansen et al. |
| 2003/0007598 A1 | 1/2003 | Zhang et al. |
| 2003/0015406 A1 | 1/2003 | Guldenfels et al. |
| 2003/0181801 A1 | 9/2003 | Lasser et al. |
| 2003/0194121 A1 | 10/2003 | Eberhard et al. |
| 2003/0212327 A1 | 11/2003 | Zhang et al. |
| 2004/0015080 A1 | 1/2004 | Kelly et al. |
| 2004/0181152 A1 | 9/2004 | Zhang |

(56) References Cited

U.S. PATENT DOCUMENTS

| | | |
|---|---|---|
| 2004/0254464 A1 | 12/2004 | Stribling |
| 2005/0113683 A1 | 5/2005 | Lokhandwalla et al. |
| 2005/0171430 A1 | 8/2005 | Zhang et al. |

FOREIGN PATENT DOCUMENTS

| | | |
|---|---|---|
| EP | 0882426 A2 | 12/1998 |
| EP | 0730431 B1 | 3/2000 |
| JP | 2003-310614 | 11/2003 |
| WO | WO 83/02053 | 6/1983 |
| WO | WO 94/21189 | 9/1994 |
| WO | WO 02/17792 A1 | 3/2002 |
| WO | WO 02/43801 A1 | 6/2002 |
| WO | WO 03/103500 A1 | 12/2003 |
| WO | WO 2004/064644 A1 | 8/2004 |

OTHER PUBLICATIONS

Buchberger, W., et al., "Incidental Findings on Sonography of the Breast: Clinical Significance and Diagnostic Workup", American Journal of Radiology (AJR) 173, pp. 921-927 Oct. 1999.

Carson, P. et al., "Lesion Detectability in Ultrasonic Computed Tomography of Symptomatic Breast Patients", Investigative Radiology, vol. 23, No. 6, pp. 421-427, Jun. 1998.

Chen et al., "Computer-aided Diagnosis Applied to US of Solid Breast Nodules by Using Neural Networks", Radiology, pp. 407-412, Nov. 1999.

Cheng et al., "Automated Detection of Breast Tumors in Ultrasonic Images Using Fuzzy Reasoning", Proceedings of the IEEE Computer Society International Conference on Image Processing vol. III, pp. 420-423, Oct. 26-29, 1997.

Dawant, Benoit M. et al., "Image Segmentation", Handbook of Medical Imaging, vol. 2; Medical Image Processing and Analysis, Sonka and Fitzpatrick, eds., Chapter 2, pp. 98-101, SPIE Press, 2000.

Foster F.S. et al. "The Ultrasound Macroseope: Initial Studies of Breast Tissue", Ultrasonic Imaging USA, vol. 6, No. 3, Jul. 1984, pp. 243,261.

Giger et al., "Computer-Aided Diagnosis in Mammography", Handbook of Medical Imaging, vol. 2: Medical Image Processing and Analysis, Sonka and Fitzpatrick, Chapter 15, pp. 915-1004, SPIE Press 2000.

Heywang-Kobrunner, Dershaw and Schreer, Diagnostic Breast Imaging, pp. 87-102, Thieme Publishers 2001.

Jackson, Valerie P., "Controversies in Ultrasound Screening", Society of Breast Imaging 5th Postgraduate Course, May 16-19, 2001, Sheraton Harbor Island, San Diego, CA, pp. 93-95, May 16, 2001.

Jalali, "Sound Combination: Ultrasound Paired With Mammography Can Improve Cancer Detection for Dense-Breasted Women", ADVANCE for Administrators in Radiology and Radiation Oncology, pp. 68-70, Mar. 1999.

Kopans, "Breast Cancer Screening With Ultrasonography", Lancet, vol. 354, pp. 2096-2097, Dec. 18-25, 1999.

Kopans, D. et al., "Whole-Breast US Imaging: Four Year Follow-Up", Radiology 157: 505-507, 1985.

Labsonics, Inc., "LABSONICS Ultrasound Breast Scanner: Accurate, High-Performance Investigation of the Breast for Confident Diagnosis", 8-page product brochure from LABSONICS, Inc., Mooresville, Indiana, 1983.

Lehman et al., "Effect of Age and Breast Density on Screening Mammograms with False-Positive Findings", American Journal of Radiology (AJR) 173: 1651-1655, Dec. 1999.

Lorad, a Hologic Company, "Fully Automatic Self-Adjusting Tilt Compression Plate", 3-page product description downloaded and printed on May 22, 2002 from www.loradmedical.com/p225.html.

Lowers, J., "Experimental Modes Abound for Detecting Breast Cancer: Vibrational Resonance Technique Among the Contenders", Women's Health Supplement to Diagnostic Imaging, pp. 15-17, Apr. 2001.

McKnoulty, L., "Ultrasound has Unique Strengths in Breast Imaging", 3-page printout from www.auntminnie.com one Mar. 1, 2002, Jan. 2002.

McSweeney, M. et al., "Whole Breast Sonography," Radiologic Clinics of North America, vol. 23, No. 1, pp. 157-167, Mar. 1985.

Medison Image Gallery, five (5) selected pages from www.medison.com, printed Oct. 10, 2001.

Mendelson, Ellen B., "Current Status of Breast US", RSNA Categorical Course in Breast Imaging, pp. 295-309, 1999.

Qayyum, A. et al., "MR Imaging Features of Infiltrating Lobular Carcinoma of the Breast: Histopathologic Correlation", American Journal of Radiology (AJR) 178: 1227-1232, May 2002.

Rahbar, G. et al., "Benign Versus Malignant Solid Breast Masses: US Differentiation", Radiology 213:889-894, 1999.

Rapp, Cynthia L., "Breast Ultrasound", Lecture Notes for EDA AHP 230-0406, Health & Sciences Television Network, Primedia Healthcare, Carrolton TX, Mar. 2000.

Richter, K. et al., "Description and First Clinical Use of a New System for Combined Mammography and Automated Clinical Amplitude/Velocity Reconstructive Imaging Breast Sonography", Investigative Radiology, vol. 32, No. 1, pp. 19-28, Jan. 1997.

Richter, K. et al., "Detection of Diffuse Breast Cancers with a New Sonographic Method", J. Clinical Ultrasound 24: pp. 157-168, May 1996.

Richter, K. et al., "Detection of Malignant and Benign Breast Lesions with an Automated US System: Results in 120 Cases", Radiology 205: pp. 823-830, Dec. 1997.

Richter, K. et al., "Differentiation of Breast Lesions by Measurements Under Craniocaudal and Lateromedial Compression Using a New Sonographic Method", Investigative Radiology, vol. 31, No. 7, pp. 401-414, Jul. 1996.

Richter, K. et al., "Quantitative Parameters Measured by a New Sonographic Method for Differentiation of Benign and Malignant Breast Disease", Investigative Radiology, vol. 30, No. 7, pp. 401-411, Jul. 1995.

Russ, "The Image Processing Handbook, 3rd Edition", CRC Press/IEEE Press, p. 264, 1998.

Schreiman, J. et al., "Ultrasound Transmission Computed Tomography of the Breast", Radiology 150; pp. 523-530, 1984.

Singh, S. and Al-Mansoori, R., "Identification of Regions of Interest in Digital Mammograms", J. Intelligent Systems10:2, 2000.

Smith, D., "Breast Ultrasound", Radiologic Clinics of North America, vol. 39, No. 3, pp. 485-497, May 2001.

"Ultrasound RSNA Preview: Productivity and Ease of Use Dominate New Ultrasound Productss", Medical Imaging, pp. 55-56, Nov. 1999.

Zonderland, H. et al., "Diagnosis of Breast Cancer: Contribution of US as an Adjunct of Mammography", Radiology 213: 413-422, 1999.

Dec. 28, 2005 International Search Report and Written Opinion in connection with International Application No. PCT/US05/19604.

European search report dated Jan. 29, 2007 in connection with European patent application No. 03 73 4336.

* cited by examiner

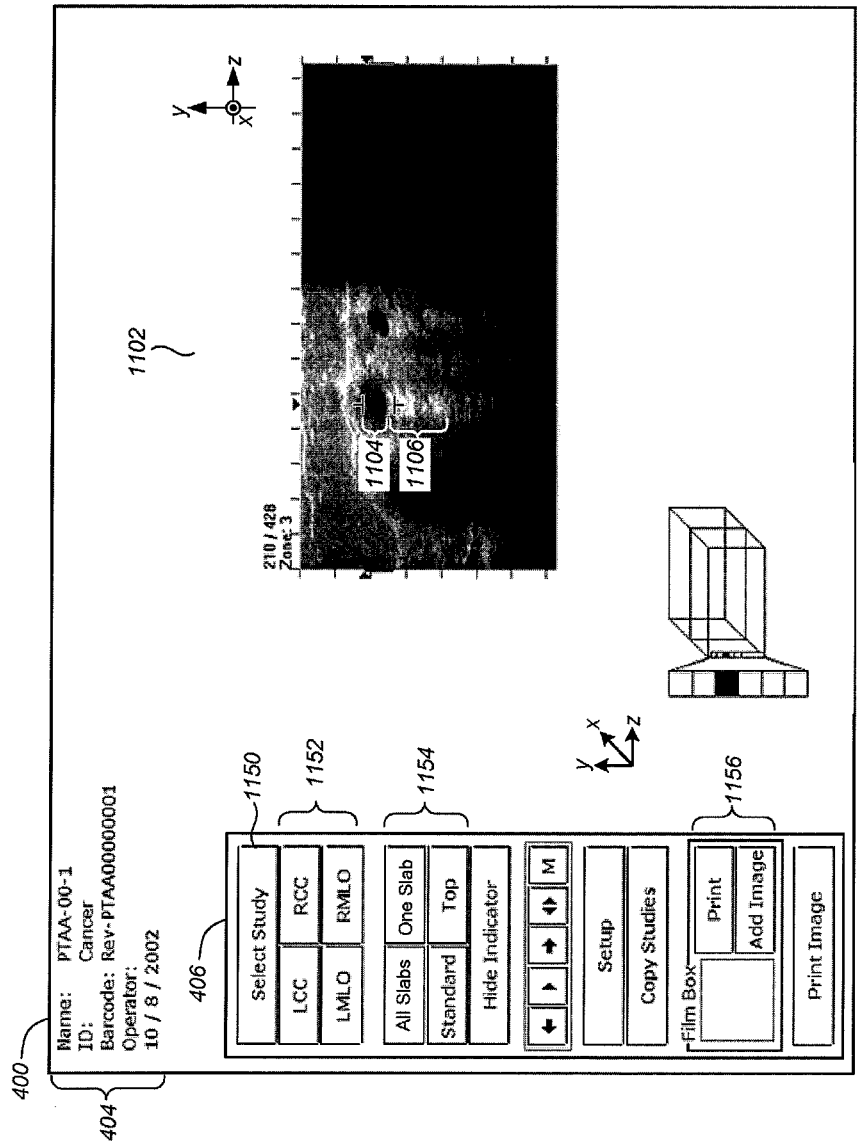

ADJUNCTIVE ULTRASOUND PROCESSING AND DISPLAY FOR BREAST CANCER SCREENING

CROSS-REFERENCE TO RELATED APPLICATIONS

This application is a Rule 1.53 (b) continuation of U.S. application Ser. No. 12/546,339 filed Aug. 29, 2009 which is a Rule 1.53(b) continuation of U.S. application Ser. No. 10/305,936, filed Nov. 27, 2002, now U.S. Pat. No. 7,597,663 which in turn is a continuation-in-part (and claims the benefit) of U.S. application Ser. No. 10/160,836, filed May 31, 2002, now U.S. Pat. No. 7,556,602, which in turn is a continuation-in-part of International Application No. PCT/US01/43237, filed Nov. 19, 2001, which in turn claims the benefit of U.S. Provisional Application No. 60/252,946, filed Nov. 24, 2000, each of these applications being incorporated by reference herein. The above-mentioned U.S. application Ser. No. 10/160,836 (and therefor this application also in turn) also claims the benefit of U.S. Provisional Application No. 60/326,715, filed Oct. 3, 2001, which is incorporated by reference herein. U.S. application Ser. No. 10/305,936 (and therefor this application in turn) also claims the benefit of U.S. Provisional Application No. 60/415,385, filed Oct. 1, 2002, the entire contents of which are incorporated by reference herein. The subject matter of U.S. application Ser. No. 10/305,936 (and therefor this application also in turn) is related to the subject matter of U.S. application Ser. No. 10/305,661, filed Nov. 27, 2002, now U.S. Pat, No. 7,103,205, which is incorporated by reference herein.

FIELD

This patent specification relates to medical imaging systems and processes. In particular, the present invention received relates to the processing and display of breast ultrasound information in a manner that efficiently and intuitively complements traditional x-ray mammogram-based breast cancer screening methods.

BACKGROUND

Breast cancer is the most common cancer among women other than skin cancer, and is the second leading cause of cancer death in women after lung cancer. The American Cancer Society currently estimates that there are about 203,500 new invasive cases of breast cancer per year among women in the United States and 39,600 deaths per year from the disease. Prevention and early diagnosis of breast cancer are of foremost importance. Because early breast cancer does not produce symptoms, the American Cancer Society recommends a screening mammogram and a clinical breast examination every year for women over the age of 40.

X-ray mammography is currently the only imaging method for mass screening of breast cancer. In health maintenance organizations (HMOs) and other medical organizations, specialized x-ray mammography clinics designed for high patient throughput are being increasingly used to screen as many women as possible in a time and cost efficient manner. Numerous studies have shown that early detection saves lives and increases treatment options. Recent declines in breast cancer mortality rates (e.g., 39,600 deaths in 2002 versus 41,200 in 2000) have been attributed, in large part, to the regular use of screening x-ray mammography.

It has been found that the use of ultrasound mammography (sonomammography) in conjunction with conventional x-ray mammography can drastically increase the early breast cancer detection rate. Whereas x-ray mammograms only detect a summation of the x-ray opacity of individual slices over the entire breast, ultrasound can separately detect the acoustic impedance of individual slices of breast tissue, and therefore may allow detection of breast lesions where x-ray mammography alone fails.

However, as discussed in Ser. No. 10/160,836, supra, despite strong evidence that use of independent ultrasound examination would improve early breast cancer detection and therefore save lives, substantial resistance against such use currently exists in the medical industry, including the radiologists themselves, and among policymakers. As used herein, the term "radiologist" generically refers to a medical professional that analyzes medical images and makes clinical determinations therefrom, it being understood that such person might be titled differently, or might have differing qualifications, depending on the country or locality of their particular medical environment. Several interrelated factors are often cited, including: (i) the false negative (missing) rate of independent ultrasound examination is unknown, (ii) the false positive rate of independent ultrasound examination is known to be very high, leading to an increase in unneeded patient callbacks and biopsies, (iii) lack of image acquisition standardization, leading to variability among different operators and radiologists, (iv) the additional time and equipment required to conduct the ultrasound examination, leading to an increase in cost, (v) most if not all radiologists are not trained to read screening ultrasound images, which contain features not found in current breast imaging textbooks or taught in current medical school courses, leading to a potential increase in false negative (missing) rate and in the additional radiologist time required to analyze the ultrasound images, and (vi) the additional training and clinical experience that would be required for the radiologist to properly analyze the ultrasound images.

Various schemes have been proposed for processing and presenting breast ultrasound information in conjunction with x-ray mammogram information for use in breast cancer detection environments. In U.S. Pat. No. 5,938,613, which is incorporated by reference herein, a method and apparatus for performing sonomammography and enhanced x-ray imaging is discussed in which ultrasound equipment is integrated with mammography equipment to generate ultrasonic images of the breast that are in geometric registration with an x-ray mammogram. An x-ray mammogram image of an immobilized breast is acquired and, while the breast is still immobilized, an ultrasound scan is acquired using an automated ultrasound probe translation mechanism. Cross-sectional ultrasonic slices are summed across the entire breast to form a two-dimensional ultrasound image, which is then overlaid onto the digitized x-ray image for viewing by the radiologist. Precise geometric registration between the ultrasound image and the x-ray mammogram is automatically provided because the breast is immobilized between imaging procedures and because the coordinates of the ultrasound probe are known during each scan. The radiologist is permitted to instantiate certain algorithms such as digital subtraction between the registered medical images.

However, the '613 patent is deficient in several respects with respect to the practical, real-world factors associated with the current resistance against the use of ultrasound in mass breast cancer screening environments. For example, the large base of currently installed x-ray imaging systems would require substantial retooling to accommodate the mechanical apparatus of the '613 patent that keeps the breast immobilized between imaging procedures and that performs the automated ultrasound scans. As another example, by displaying a summation ultrasound image of all breast slices together, the '613 method deprives the radiologist of the ability to view individual planes inside the breast. More generally, the computer-registered, static overlay of the summation ultrasound image onto the x-ray image affords only a limited amount of ultrasonic information to the radiologist as compared to the actual amount of ultrasonic data actually acquired, and affords only limited perception by the radiologist of structures within the breast.

In U.S. Pat. No. 5,662,109, a method and system for multi-dimensional imaging and analysis for early detection of diseased tissue is discussed. Ultrasound scans of a breast are processed into multiple layers of two-dimensional images, thus yielding a three-dimensional data set. This data set and a two-dimensional x-ray mammogram are input to an enhancer that performs one or more "data fusion" algorithms to generate a three-dimensional representation of the breast for viewing. The enhancer includes a registration module that expands and/or reduces dimensions of the data to register and align the ultrasound and mammographic images.

However, it is not believed that the various three-dimensional views of the "fused" data discussed in the '109 patent, such as the perspective view shown in FIG. 1 thereof, would be useful to a typical radiologist-trained in conventional x-ray mammography methods. As described supra, radiologists typically spend many years developing expertise in analyzing a very particular set of two-dimensional x-ray mammographic data taken from standardized views, most commonly the craniocaudal (CC) and mediolateral oblique (MLO) views. It is believed that most radiologists would be reluctant to "start over again" with an entirely new, different way of viewing the complex structures of a breast, and that the medical industry would likewise be reluctant to force radiologists to accept these viewing methods.

In view of the above discussions, it would be desirable to provide an adjunctive ultrasound mammography system that integrates ultrasound mammography into current breast cancer screening methodologies.

It would be further desirable to provide an adjunctive ultrasound mammography system that displays breast ultrasound information in a manner that facilitates the radiologist's perception of internal breast structures that may not be readily apparent in an x-ray mammogram, while also being able to confirm the radiologist's perception of internal breast structures that are apparent in the x-ray mammogram.

It would be even further desirable to provide an adjunctive ultrasound mammography system that displays breast ultrasound information in a manner that supplements, rather than replaces, conventional x-ray mammogram viewing methods, thereby increasing the likelihood of adoption by both individual radiologists and the medical industry.

It would be even further desirable to provide an adjunctive ultrasound mammography system that takes little or no special familiarization or training from the radiologist in order to effectively view breast ultrasound information.

It would be still further desirable to provide an interactive user interface for an adjunctive ultrasound mammography system that allows the radiologist to quickly and intuitively navigate among different representations of the breast ultrasound information.

It would be even further desirable to display such breast ultrasound information in a manner that allows benign features to be more easily dismissed by the viewing radiologist.

SUMMARY

An adjunctive ultrasound mammography system and associated methods are provided including an intuitive, interactive user interface for displaying breast ultrasound information to a user. According to a preferred embodiment, an array of thick-slice images derived from volumetric ultrasound scans of a breast is displayed, each thick-slice image representing a thick-slice or slab-like region of the breast volume substantially parallel to a standard x-ray mammogram view of the breast. Responsive to a first single-click or single-movement user selection of a first point on one of the thick-slice images, an enlarged view of that thick-slice image is displayed with a cursor positioned at a corresponding point. Responsive to a second single-movement user selection of a second point on the enlarged view, a first planar ultrasound image encompassing the second point is displayed, the first planar ultrasound image representing the volumetric ultrasound scans along a first plane substantially nonparallel to, and preferably perpendicular to, the orientation of the slab-like region for that thick-slice image.

According to another preferred embodiment, a second planar ultrasound image is shown concurrently with the first planar ultrasound image representing the volumetric scans along a second plane substantially orthogonal to both the first plane and to the orientation of the slab-like region. According to another preferred embodiment the first and second planar ultrasound images are displayed concurrently with the enlarged thick-slice image or the array of thick-slice images. The first and second planes correspond to the current cursor position on an active one of the thick-slice images and are updated in real time as the cursor is moved. Range markers are provided on the planar ultrasound images corresponding to the current cursor position and to the borders of the slab-like region for the active thick-slice image.

According to another preferred embodiment, first and second plane indicators are displayed on the active thick-slice image, the plane indicators corresponding to the first and second planes and appearing as straight lines for a default configuration in which the first and second planes are orthogonal to each other and to the orientation of the slab-like region for the active thick-slice image. In the default configuration, the first and second plane indicators intersect the cursor on the active thick-slice image. The user is permitted to depart from the default configuration if desired by moving the first and second plane indicators in a manner analogous to the way lines are moved in a computer-aided drawing system, while the first and second planes and the first and second planar ultrasound images are updated in real time to correspond to the orientations and locations of the first and second plane indicators.

A user interface according to the preferred embodiments is preferably provided in conjunction with an x-ray mammogram viewer such that the array of thick-slice ultrasound images is displayed in coordination with a corresponding x-ray mammogram image taken from the same standard x-ray mammogram view. The x-ray mammogram image, which is preferably provided on a backlighted film display but which can alternatively be provided on an electronic display, is displayed in close proximity to the array of thick-slice ultrasound images to allow easy back-and-forth viewing. Preferably, the thick-slice images are displayed at full scale on an LCD monitor positioned directly below the x-ray mammogram images, while the first and second planar ultrasound images are displayed on smaller CRT displays positioned to the sides of the LCD monitor. However, a variety of different configurations having differing advantages are within the scope of the preferred embodiments as described further infra.

According to one preferred embodiment, the displayed thick-slice images are inverted to represent high acoustic reflections as "dark" and low acoustic reflections as "bright," in distinction to a standard ultrasound display convention in which low acoustic reflections are displayed as "dark" and high acoustic reflections are displayed as "bright." Preferably, the breast area is digitally segmented from the surrounding area, and the surrounding area is reset to "dark" prior to display of the inverted thick-slice image. The inverted thick-slice images are of more familiar significance to radiologists having years of expertise in analyzing conventional x-ray mammograms. For example, the inverted thick-slice images allow benign features to be more easily dismissed as compared to non-inverted thick-slice images.

According to another preferred embodiment, a method for computing the thick-slice images from the volumetric ultrasound representation of the breast is provided, each thick-slice image pixel being computed based on the statistics of a voxel column passing through that location from a lower border to an upper border of the relevant slab-like region. In particular, the statistical properties of interest are ones that incur changes across different pixel locations in mass localities that are more significant for masses greater than a preselected size of interest and that are less significant for smaller masses. Accordingly, mass lesions greater than the preselected size of interest are emphasized while smaller mass lesions are de-emphasized in the resulting thick-slice image. In one preferred embodiment, the thick-slice pixel value is selected as that value for which a cumulative distribution function (CDF) of the voxel column becomes equal to a threshold value, the threshold value being a predetermined fraction of a ratio of the preselected size of interest to the distance between the first and second border planes. A method for ensuring the visibility of lesions straddling the borders between adjacent thick-slice regions is also provided in which (i) an actual result for the actual thick-slice region is computed, (ii) a hypothetical result is computed for a hypothetical thick-slice region that is partially elevated into the adjacent thick-slice region, and (iii) resetting the actual result to the hypothetical result if the hypothetical result is more indicative of lesser ultrasound reflections.

BRIEF DESCRIPTION OF THE DRAWINGS

FIG. 11 illustrates an adjunct ultrasound display according to a preferred embodiment presenting a raw ultrasound image;

DETAILED DESCRIPTION

Figure 1:
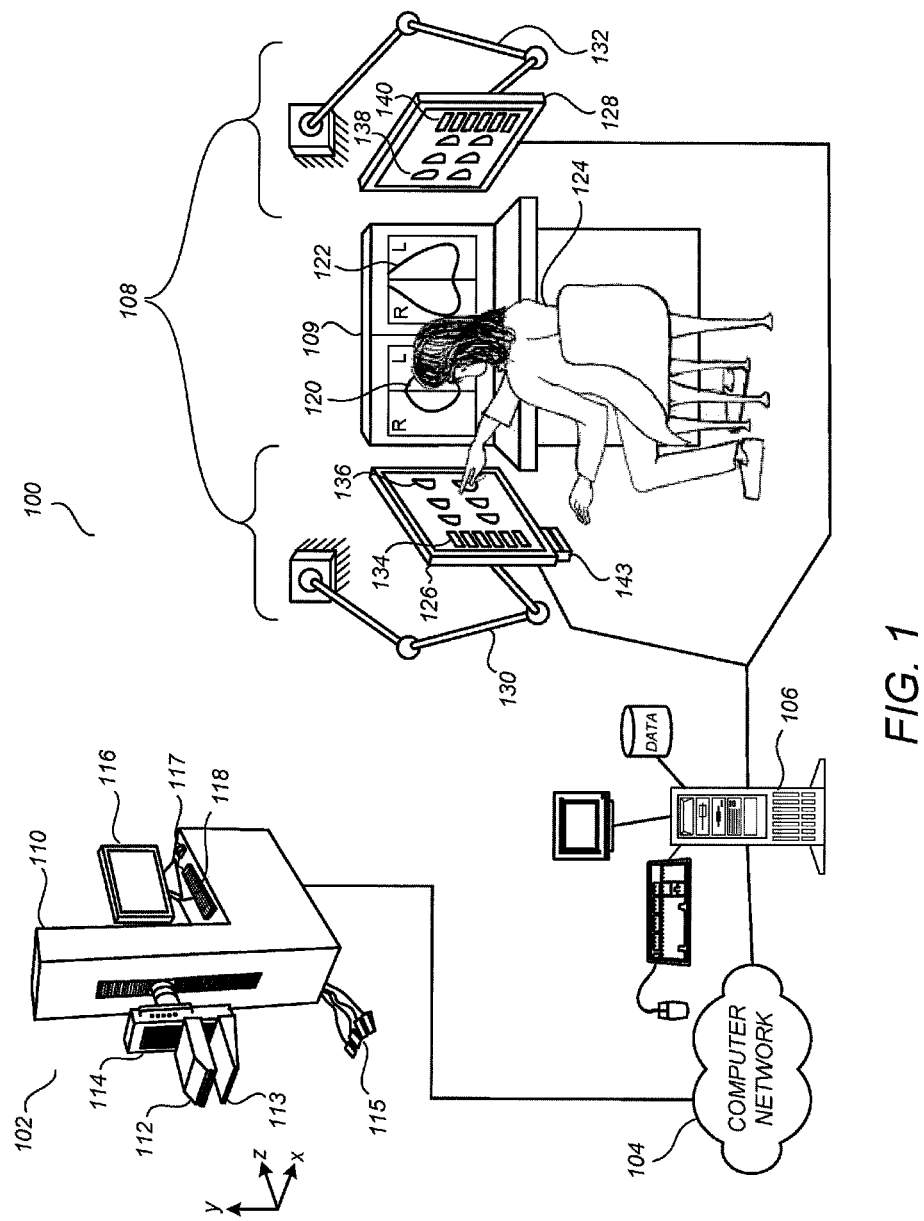
FIG. 1 illustrates a conceptual diagram of a system and method for breast cancer screening using adjunctive ultrasound mammography according to a preferred embodiment.

FIG. 1 illustrates a conceptual diagram of a system 100 and associated methods for breast cancer screening using adjunctive ultrasound mammography according to a preferred embodiment. Adjunctive ultrasound mammography refers to the acquisition and display of breast ultrasound information during the breast cancer screening process in a manner that supplements x-ray mammogram information. System 100 comprises an ultrasound scanning station 102, a computer network 104, an adjunctive ultrasound server 106, and an adjunctive ultrasound screening station 108.

Ultrasound scanning station 102 comprises an apparatus designed to flatten and immobilize a breast while volumetric ultrasound scans are acquired. The breast is flattened along a plane substantially parallel to a standard x-ray mammogram view plane such as the CC and MLO view planes, although the ultrasound scanning station 102 is capable of flattening the breast along a variety of other planes as well. Ultrasound scanning station 102 comprises a housing 110 movably supporting a gantry 114, the gantry 114 in turn supporting an upper compression/scanning assembly 112 and a lower compression plate 113 in a vertically movable manner.

For clarity of description herein, the y direction represents the head-to-toe direction with respect to the patient, the x-axis represents the left-to-right direction, and the z direction extends outward from the chest wall. The x-y, y-z, and x-z planes thus correspond to the coronal, sagittal, and axial planes, respectively. The patient may stand or sit in front of the ultrasound scanning station 102, facing the +z direction in FIG. 1, with one breast placed between the upper compression/scanning assembly 112 and lower compression plate 113. Responsive to control by an operator using foot pedals 115, a keyboard 118, a mouse 117, buttons on the gantry 114, and/or other input methods, the breast is compressed and an ultrasound probe head (not shown) contained inside upper compression/scanning assembly 112 is linearly translated over the top of the breast while two-dimensional ultrasound slices are acquired. Ultrasound scanning station 102 further comprises an ultrasound processor (not shown) coupled to the ultrasound probe head that receives the acoustic echo signals and forms the two-dimensional ultrasound slices therefrom. The ultrasound slices may be viewed in real-time on a monitor 116 as they are generated, the monitor 116 also serving as an interface display for controlling of the overall operation of the ultrasound scanning station 102.

Preferably, the upper compression/scanning assembly 112 is similar to that described in Ser. No. 60/415,385, supra. The breast skin surface contacts one side of a taut sheet of acoustically transparent material such as Mylar® while the other side of the taut sheet is in actual or imminent contact with the probe head. Acoustic coupling between the taut sheet and the probe head is facilitated by a stream, drip, or bath of water or other low-viscosity, acoustically conductive fluid. The gantry 114 is rotatable in a plane parallel to the coronal plane of the patient, i.e., around the z-axis in FIG. 1, such that scans of the breast flattened along the MLO plane or other view planes can be achieved. The gantry 114 can also be tilted forward or backward relative to the patient, i.e., around the x-axis in FIG. 1, between a range of roughly plus 30 degrees to minus 30 degrees.

According to one preferred embodiment, a breast scan for a given view is acquired by a single sweep of the probe contained within upper compression/scanning assembly 112. In this case, it is required that the scan penetration depth extend as far as possible toward the lower compression plate. For larger breasts, this can be 6 cm or greater, in which case a lower probe frequency is required and a correspondingly lesser resolution is obtained than for high-frequency scans. According to another preferred embodiment, dual sweeps can be taken for a given view, with the gantry being rotated 180 degrees around the y-axis in FIG. 1 between sweeps. In this case, the scans only need to penetrate through half the breast thickness and so a higher scan frequency can be used. The resulting ultrasound "half-slices" from the first and second sweeps can then be stitched together to form complete slices. In still another preferred embodiment, the lower compression plate 113 is replaced with a second compression/scanning assembly including a second probe head. In this case the separate upper and lower probe sweeps can be achieved without requiring the intermediate 180 degree rotation of the gantry, and issues relating to registration between the half-slices are avoided.

During or after the ultrasound scanning process, the raw ultrasound data is provided across the computer network 104 to the adjunctive ultrasound server 106, where the raw ultrasound data is processed into adjunctive ultrasound data that will be made available to the screening radiologist, the adjunctive ultrasound data including ultrasound slices, thick-slice images, CAD outputs, and other useful information. It is to be appreciated that the processing of the raw ultrasound data into the adjunctive ultrasound data may be performed by any of a variety of different computing devices coupled to the computer network 104 and then transferred to the adjunctive ultrasound server 106.

In current mass breast cancer screening environments based on x-ray mammography, a screening radiologist 124 examines x-ray mammograms for many patients en masse in a single session using an x-ray viewing station 109. The x-ray viewing station 109 may range from a simple light box, as in FIG. 1, to more complex x-ray CAD workstations that automatically move the x-ray mammograms past the radiologist 124 on a conveyor belt as a nearby CAD display highlights suspicious areas of the mammogram. Almost universally, left and right CC x-ray views 120 are positioned on one side of the x-ray viewing station 109, and left and right MLO x-ray views 122 are positioned on the other side. The radiologist 124 quickly examines the x-ray mammograms. For some x-ray mammograms the radiologist needs only a few seconds, while for other x-ray mammograms the radiologist needs up to five minutes, with an average being about two minutes per mammogram.

According to a preferred embodiment, this existing arrangement remains substantially undisturbed, but is augmented with equipment and data that facilitates fast and thorough x-ray mammogram screening by giving the radiologist a quick ultrasonic "second look" at the internal breast structure. Adjunctive ultrasound screening station 108 comprises first and second adjunct displays 126 and 128 conveniently positioned near the x-ray viewing station 109 such that the radiologist 124 can (i) easily look back and forth between the first adjunct display 126 and the CC x-ray views 120, and (ii) easily look back and forth between the second adjunct display 128 and the MLO x-ray views 122. Preferably, adjunct displays 126 and 128 display thick-slice images 136 and 138, respectively, corresponding to thick-slice regions of the breast volume substantially parallel to the CC and MLO view planes, respectively, acquired while the breast was flattened along the CC view plane and the MLO view plane, respectively. This allows the spatial content of the thick-slice images to roughly correspond to the spatial content of the corresponding x-ray mammograms, facilitating ready comparisons therebetween. However, the scope of the preferred embodiments is not necessarily so limited. According to an alternative preferred embodiment, the benefits of meaningful "second look" information inside the breast structure is still provided even where (i) the breast is compressed along a non-standard plane during the volumetric scans, or (ii) the breast is not compressed at all during the volumetric scans, or (iii) the thick-slice images correspond to planes not parallel to a standard x-ray mammogram view plane. In view of the thick-slice segmentation and inversion process described herein and other features and advantages according to the preferred embodiments, such non-standard compressions or non-standard thick-slice planes can still result useful thick-slice adjunctive ultrasound images for viewing, especially where a spatial guide similar to the iconic representations infra are displayed to properly "orient" the reader to the position and orientation of the non-standard thick-slice image.

According to a preferred embodiment, adjunct displays 126 and 128 are designed to facilitate quick, intuitive, and interactive navigation among different views of the thick-slice images and other adjunctive ultrasound data. Adjunct displays 126 and 128 are preferably touch-screen displays but other input devices just as a PC keyboard and mouse (not shown) can be used. FIG. 1 also shows control buttons 134 and 140 on adjunct displays 126 and 128, respectively, that have layouts and functionalities described further infra. A bar code reader 143 reads a bar code of the x-ray mammogram, wherein the associated adjunctive ultrasound data for that breast is automatically retrieved from the ultrasound server 106. In the event that the x-ray mammograms are loaded onto a motorized viewer, the bar codes from the x-ray mammograms are read as the images are loaded into the apparatus by a technician. Alternatively, the user can scan the bar code directly from the x-ray mammogram when it appears in front of them using a hand-held bar code scanner, wherein the corresponding adjunctive ultrasound data is retrieved from the adjunctive ultrasound server 106. For clarity of presentation, the user interface description herein is presented relative to the CC adjunct display 126, it being understood that analogous descriptions apply to the MLO adjunct display 128 or to non-standard-plane adjunct displays in general. Additionally, although most of the exemplary displays herein show the CC data for a single breast (left or right), it is to be appreciated that concurrent viewing of the CC data for the other breast on the same display, or combinations of CC/MLO/non-standard views for both left and right breasts, are clearly within the scope of the preferred embodiments.

The adjunct display 126 of FIG. 1 contains an array of smaller, or thumbnail, thick-slices images 136, with the terms small and thumbnail simply indicating that the images are small enough to fit on the same monitor while communicating structures of more than one thick-slice region of the breast, and are smaller in size than the enlarged versions. Due to practical display size limitations, it is expected that the small or thumbnail images will be less than full-scale images and the enlarged versions will be greater than full-scale, although the scope of the preferred embodiments is not so limited. In one alternative preferred embodiment both the thumbnail and enlarged versions are less than full-scale, while in another preferred embodiment the thumbnail images are at full-scale and the enlarged versions are greater than full-scale, while in still another alternative preferred embodiment the thumbnail and enlarged versions are both greater than full-scale.

As described in Ser. No. 10/160,836, supra, the thickness of the slab-like or thick-slice volume corresponding to each thick-slice image may lie, for example, in the range of 2 mm to 20 mm, although the scope of the preferred embodiments is not so limited, and thicknesses in the range of 7 mm to 12 mm are likely to be suitable for most breast cancer screening purposes. Techniques for integrating the component ultrasound slices into thick-slice images according to the preferred embodiments include arithmetic averaging, geometric averaging, reciprocal averaging, exponential averaging, and other averaging methods, in each case including both weighted and unweighted averaging techniques. Other suitable integration methods may be based on statistical properties of the population of component ultrasound slices at common locations, such as maximum value, minimum value, mean, variance, or other statistical algorithms One particularly suitable algorithm for generating thick-slice images from a volumetric representation of a breast is described infra with respect to FIGS. 12-13.

Figure 2:
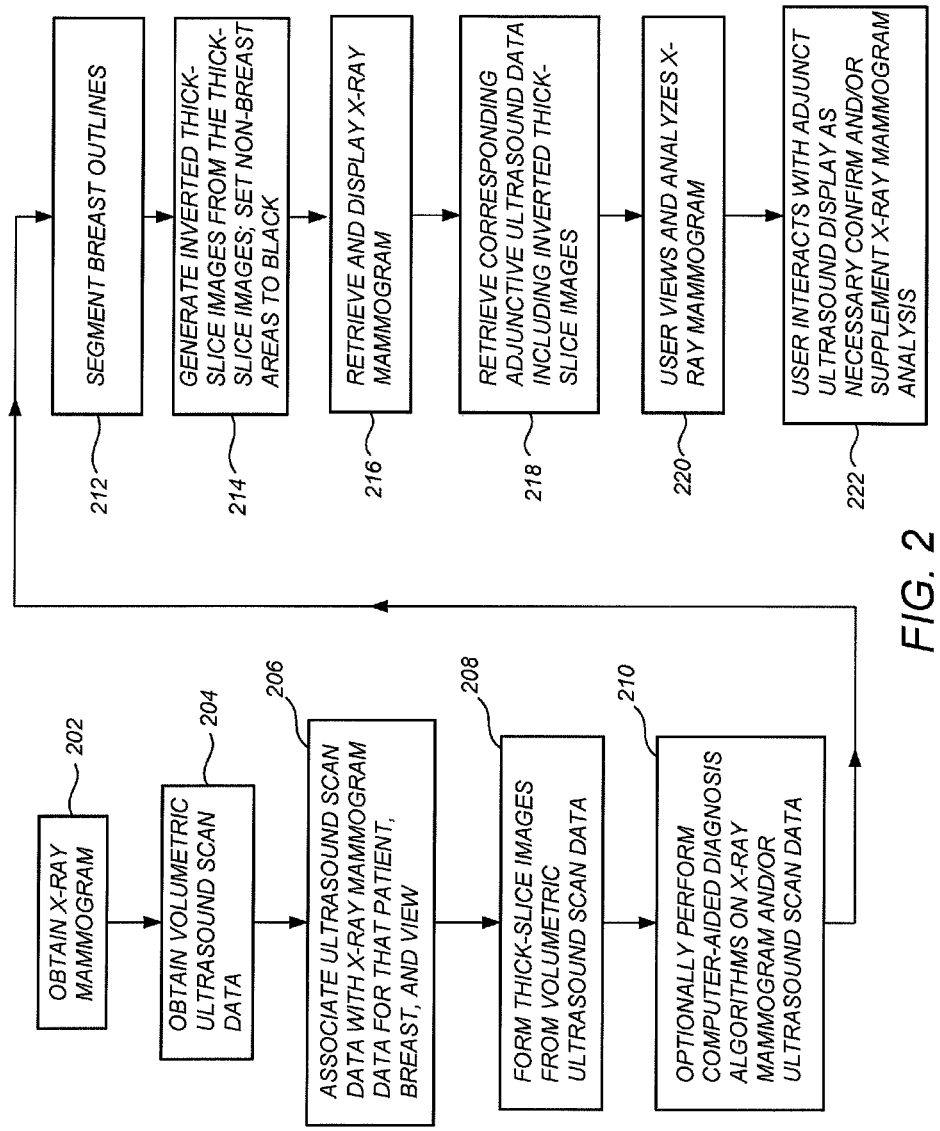
FIG. 2 illustrates steps for breast cancer screening using adjunctive ultrasound mammography according to a preferred embodiment.

FIG. 2 illustrates steps for breast cancer screening using adjunctive ultrasound mammography according to a preferred embodiment. At step 202 an x-ray mammogram is obtained and at step 204 volumetric ultrasound scan data is obtained. At step 206 the ultrasound scan data is associated with the x-ray mammogram data for the patient, breast, view, date, etc., as generally described in parent application Ser. No. 10/160,836, supra. At step 208 thick-slice images are formed from the volumetric ultrasound scan data according to the method described infra with respect to FIGS. 12-13. For CC thick-slice images, i.e., thick-slice images representing thick-slice volumes substantially parallel to the CC plane, each thick-slice image is a scalar function of coordinates (x,z). At step 210 an optional step is performed wherein computer-aided diagnosis (CAD) algorithms are applied to the ultrasound scan data and/or x-ray mammogram data. In accordance with a preferred embodiment, the resulting CAD markers may be superimposed upon one or more of the thick-slice images described throughout this application, on any of planar ultrasound views, on any of the x-ray mammogram views, or any combination of them to achieve a CAD-enabled display.

At step 212 the breast tissue is segmented from outlying areas using any of a variety of known segmentation algorithms. Preferably, a three-dimensional segmentation algorithm is performed directly on the three-dimensional volumetric scan data, although in other preferred embodiments a two-dimensional segmentation algorithm is separately applied to each thick-slice image. The segmentation step 212 results in a mask for each thick-slice image identifying the breast tissue boundary.

At step 214 inverted thick-slice images are computed from the ordinary or non-inverted thick-slice images. As used herein, a non-inverted or ordinary thick-slice image generally conforms to a standard medical ultrasound display convention in which readings of lesser acoustic reflections are displayed as "darker" (blacker, dimmer, darker gray, lower-intensity, etc.) and in which readings of higher acoustic reflections are displayed as "brighter" (whiter, lighter, higher-intensity, etc.). An inversion algorithm converts each non-inverted thick-slice image pixel $P_O(x,z)$ into a complementary or inverted value $P_{INV}(x,z)$ that is then "brighter" in regions of lesser acoustic reflection and "darker" in regions of higher acoustic reflection.

It has been found that displaying inverted thick-slice images can substantially enhance the viewing and screening process, and can facilitate the dismissal of benign lesions better than a display of non-inverted thick-slice images. This is at least because, for inverted thick-slice images, differential viewing of breast lesions versus surrounding tissue structures is provided on a similar basis as that for x-ray mammograms. For example, most radiologists have developed years of expertise in differentiating "bright" lesions from surrounding ligaments on x-ray mammograms, the surrounding ligaments also being "bright" but having different visual cues. The use of inverted thick-slice images allows their years of expertise to be extended over to the thick-slice ultrasound data, in contradistinction to the conventional ultrasound display method that would require the difficult task of differentiating "dark" lesions based on different visual cues than "dark" surrounding ligaments.

Although any of a variety of inversion algorithms could be used in accordance with the preferred embodiments at step 214, it has been found beneficial to use an inversion algorithm that also performs some degree of contrast-enhancement when mapping the darker values of $P_0(x,z)$ into the brighter values of $P_{INV}(x,z)$. For an exemplary situation in which the display monitor pixels are brightest at value 255 and lowest at value 0, one particularly suitable algorithm is given in Eq. (1) below, with γ ("gamma") being set to 0.5:

$$P_{INV}(x, z) = 255\left(\frac{255 - P_0(x, z)}{255}\right)^{1/\gamma} \quad \{1\}$$

Figure 8:
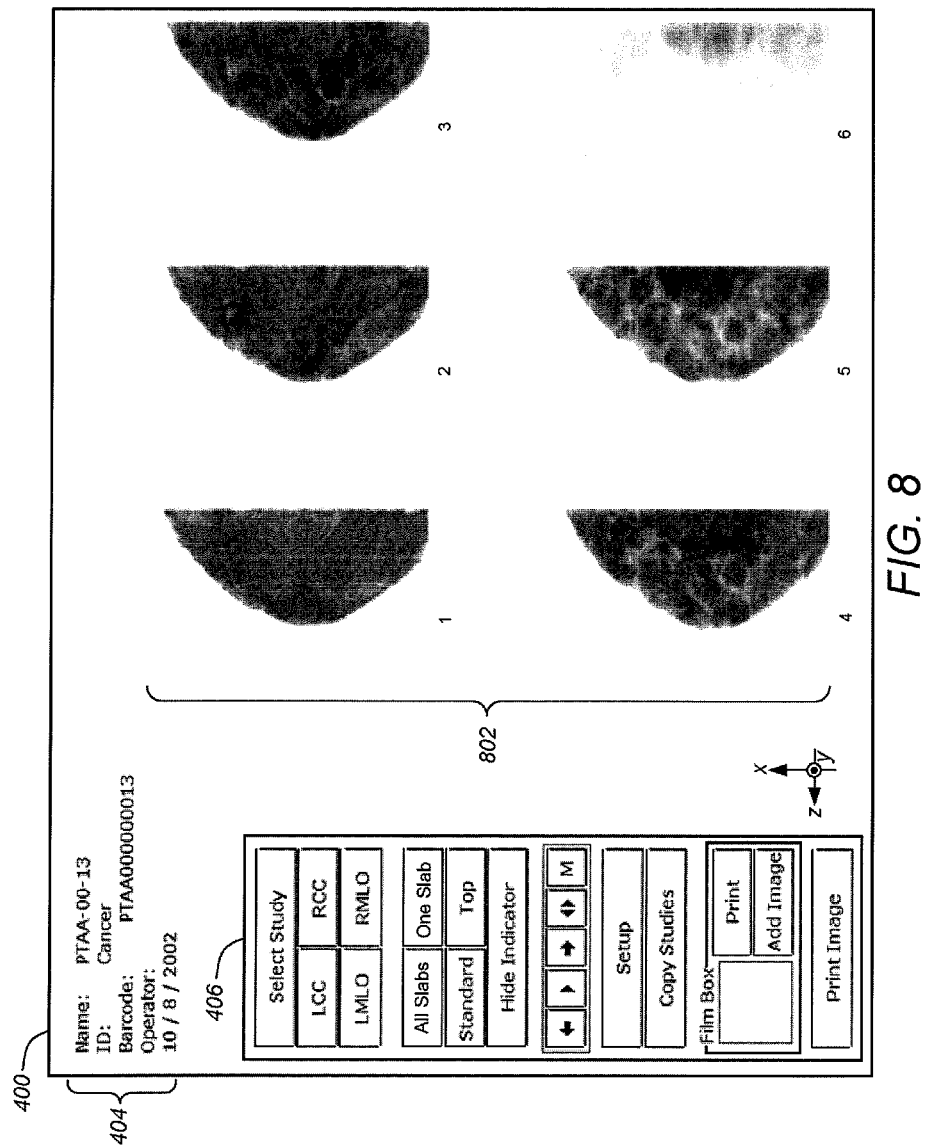
FIG. 8 illustrates an adjunct ultrasound display according to a preferred embodiment presenting an array of inverted but non-segmented thick-slice images for the same breast as FIGS. 4 and 7.

During image inversion, non-breast areas of the thick-slice images, which are initially dark, are converted to bright as displayed in the example of FIG. 8, infra. According to a preferred embodiment, the non-breast areas of the thick-slice images, as identified by the masks previously computed at step 212, are reset to dark. This step is performed so that the displayed thick-slice images are more reminiscent of an x-ray mammogram, which is dark in the unexposed regions lying outside the breast. It is to be appreciated, however, that this step can be skipped without departing from the scope of the preferred embodiments, as some users may end up preferring the white background.

Generally speaking, the ultrasound processing steps 208-214 are usually not performed in real-time, but rather are performed during an interval between the scanning process and viewing process, which can be a period of several hours or more. However, the scope of the preferred embodiments is not so limited, and the steps 202-214 may also be performed in real-time if practicable in a given clinical setting.

At step 216 the x-ray mammogram information is retrieved and displayed to the user. At step 218 the corresponding adjunctive ultrasound data is retrieved, including the inverted thick-slice images. At step 220 the user views and analyzes the x-ray mammogram image. In a manner analogous to FDA-approved practices for "second-look" x-ray mammogram CAD results, the user should first examine the x-ray mammogram without reference to the thick-slice images, first arriving at an independent conclusion based on the x-ray mammograms alone. Only after the independent x-ray mammogram analysis should the user view the thick-slice images (step 222), wherein the user interacts with the adjunct ultrasound display as necessary to confirm and/or supplement the x-ray mammogram analysis. Optionally, to ensure the proper order of viewing, the thick-slice images are withheld from view until the user verifies that an independent x-ray mammogram analysis is completed by pressing, for example, a confirmation toggle button or entering an appropriate user command.

Figure 3:
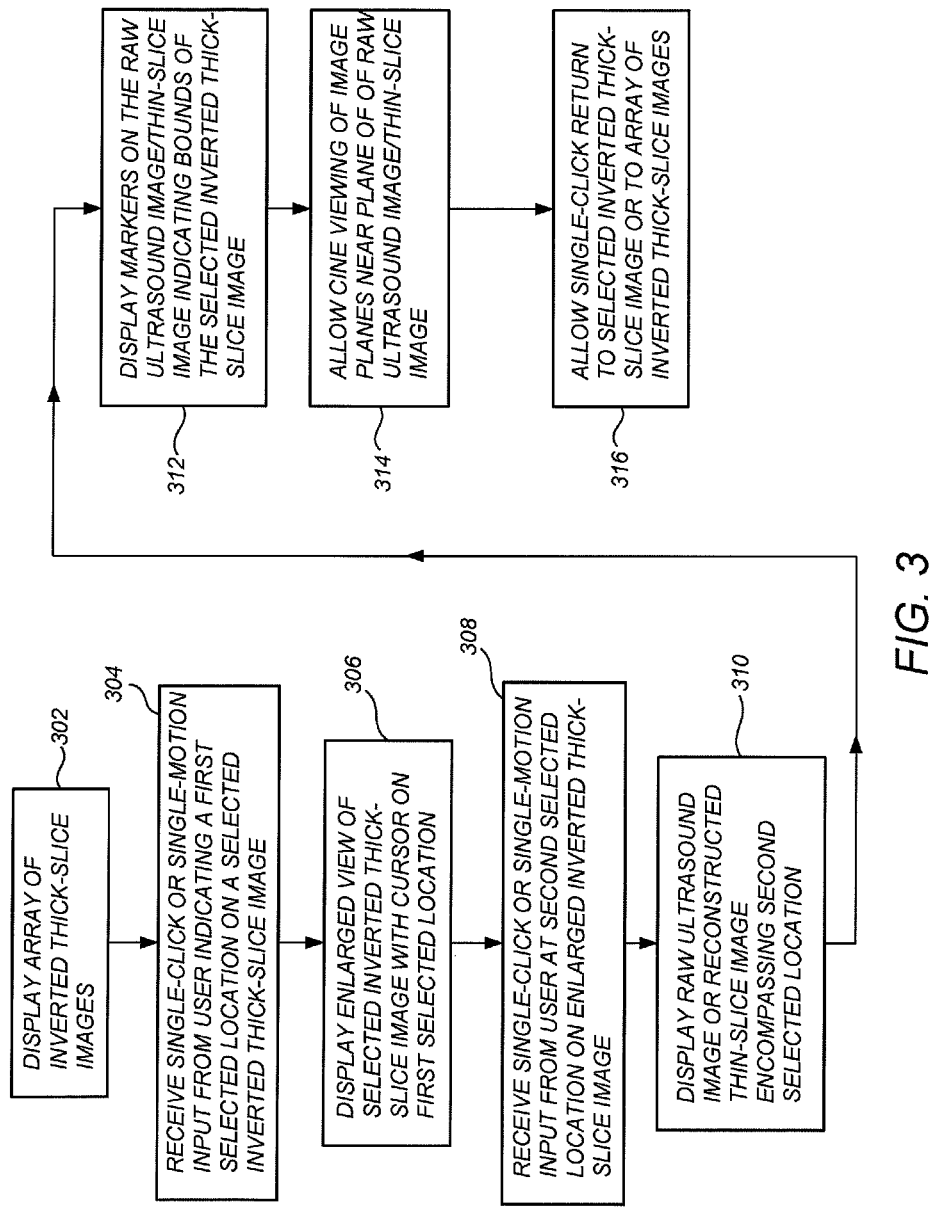
FIG. 3 illustrates steps for interactively displaying adjunctive ultrasound mammography information to a user according to a preferred embodiment.
Figure 4:
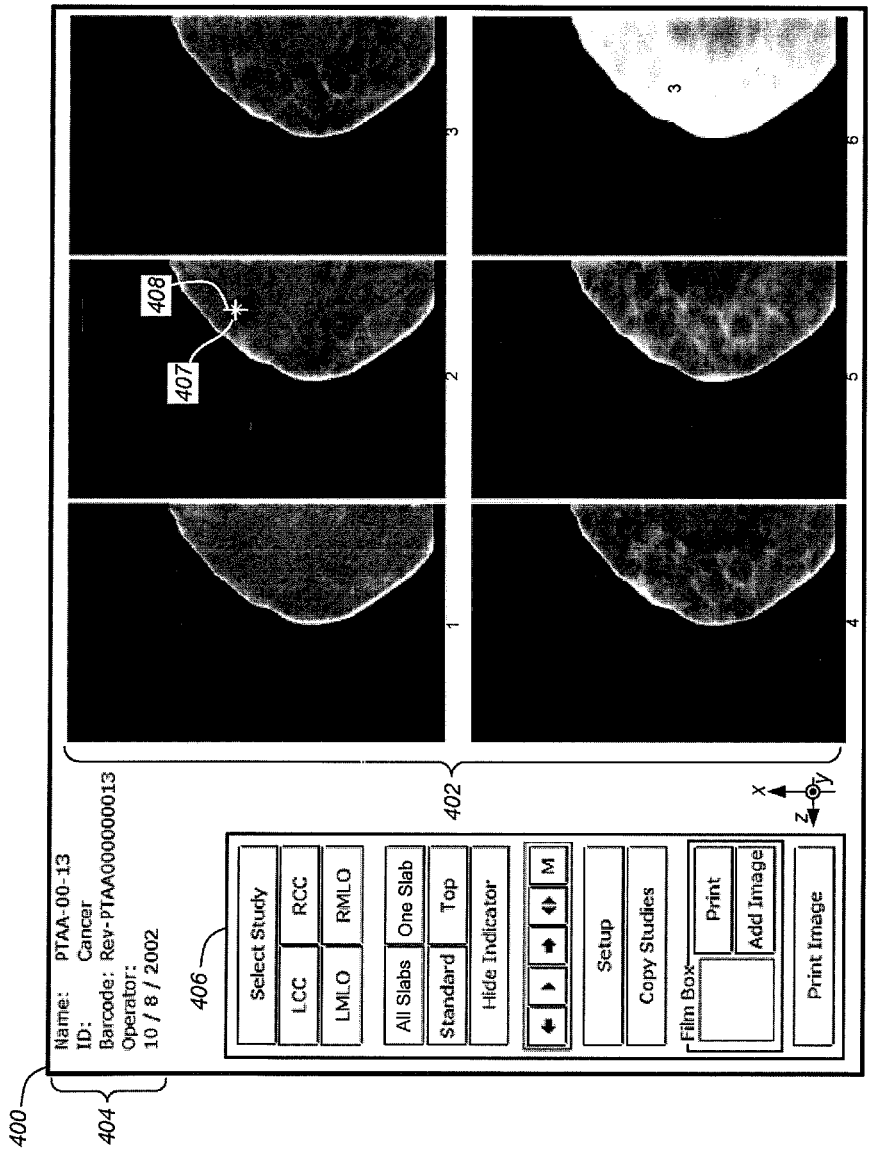
FIG. 4 illustrates an adjunct ultrasound display according to a preferred embodiment presenting an array of inverted thick-slice images.
Figure 5:
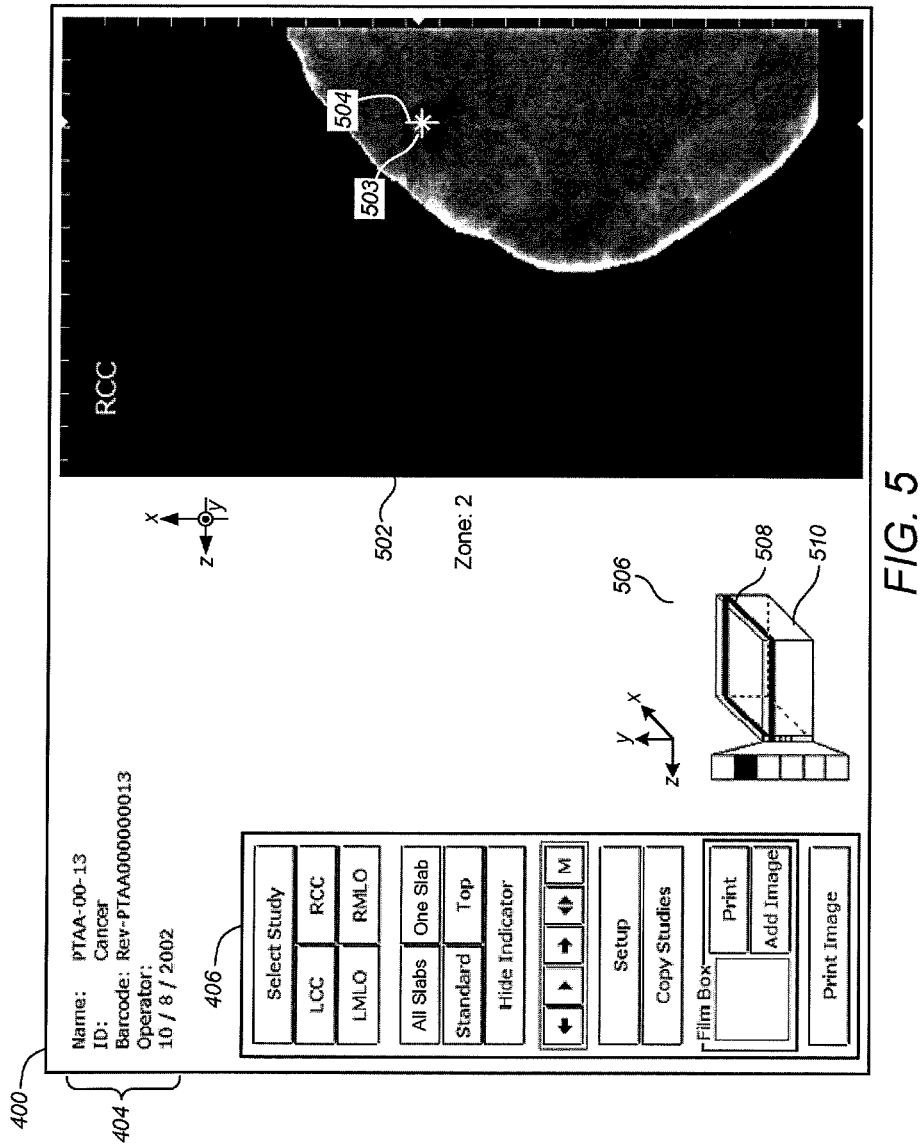
FIG. 5 illustrates an adjunct ultrasound display according to a preferred embodiment presenting an enlarged inverted thick-slice image.
Figure 6:
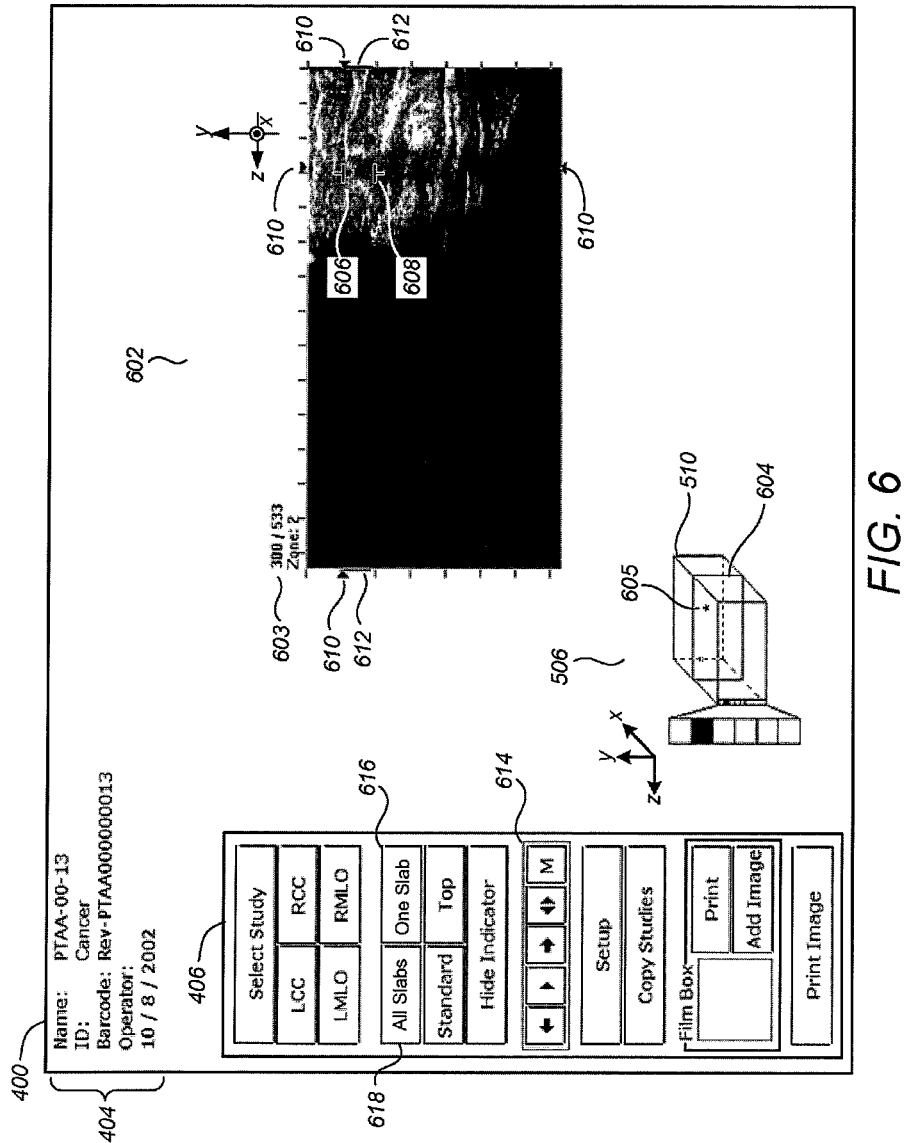
FIG. 6 illustrates an adjunct ultrasound display according to a preferred embodiment presenting a planar ultrasound image.

FIG. 3 illustrates steps for interactively displaying adjunctive ultrasound mammography information to a user according to a preferred embodiment. FIGS. 4-6 illustrate an adjunct display screen 400 at particular stages during the steps of FIG. 3. At step 302 an array of inverted thick-slice images is displayed. FIG. 4 illustrates an example of a thick-slice image array 402 on the adjust display screen 400. Adjunct display screen 400 further comprises a patient ID section 404 comprising patient identification and other relevant information. Adjunct display screen 400 further comprises a control button array 406 comprising buttons that can be actuated by a touchscreen press or a mouse/trackball inputs. Also shown in FIG. 4 is a selection marker 407 appearing at a location 408 superimposed on a thick-slice image 410. If a mouse/trackball input is used, the default mouse pointer changes to the selection marker 407 when guided over any one of the thick-slice images 402.

At step 304 a single-click or single-motion input from the user is received indicating a first selected location on a selected inverted thick-slice image. With reference to FIG. 4 this is achieved by making a mouse click with the selection marker 407 at the current position (408) or by pressing the touchscreen at position 408. In the case of a touchscreen, it is recommended that a pointing device finer than a human finger be used, such as the stylus of a personal digital assistant (PDA), to touch the screen at the location 408. Responsive to the single-click or single-motion input, at step 306 an enlarged view 502 of the selected inverted thick-slice image 410 is displayed. A selection marker 503 is displayed at a location 504 that corresponds to the same relative position on the breast as the location 408 on the thick-slice image 410.

Also shown in FIG. 5 is a three-dimensional icon 506 that roughly illustrates the thickness, location, and orientation of the thick-slice volume corresponding to the thick-slice image 502. In particular, the iconic thick-slice volume 508 is shown relative to an iconic rectangular solid 510 that roughly corresponds to the compressed breast. Although not illustrated as such in FIG. 5, it is preferable to display an iconic frame that more closely resembles a perspective view of the breast rather than the iconic rectangular solid 510. The iconic frame can comprise a three-dimensional rendering of a semi-transparent breast, and the iconic thick-slice volume 508 can be suspended at the appropriate location and orientation therein. Because the three-dimensional icon 506 does not provide any specific diagnostic information to be relied upon, it is not necessary for the iconic frame to be a perfect replica of the actual scanned breast. However, to increase the intuitiveness of the display, especially to new users, it is preferable that the semi-transparent rendering be of at least sufficient quality to be recognizable as a breast volume.

At step 308 a second single-click or single-motion input is received from the user indicating a second selected location on the enlarged inverted thick-slice image. By default, the second selected location is at the same point relative to the enlarged inverted thick-slice breast as the first selected location was to the thumbnail or smaller thick-slice image, unless the user affirmatively moves the selection marker 503 prior to clicking. In the example of FIGS. 4-6, the second selected location is at location 504 of FIG. 5. At step 310 a raw ultrasound image or reconstructed thin-slice image encompassing the second selected location is displayed.

FIG. 6 illustrates a raw ultrasound slice 602 displayed responsive to the second single-click or single-motion input. The raw ultrasound slice 602 is preferably shown in a standard, non-inverted format because this direct form of ultrasound viewing is already familiar to most users. However, it is within the scope of the preferred embodiments for the raw ultrasound slice 602 to be inverted prior to display. The raw ultrasound slice 602 represents one example of a planar ultrasound image representing sonographic properties of the breast along a plane cutting through the breast. In particular, the raw ultrasound slice 602 represents a first planar ultrasound image representing values along a first plane perpendicular to the orientation of the thick-slice region corresponding to the thick-slice image being displayed, wherein the first plane is also parallel to an ultrasound scan plane of the ultrasound probe that is swept across the breast during the volumetric scanning process. Most examples of planar ultrasound images described herein are raw ultrasound slices or orthogonal thin-slice images, the orthogonal thin-slice images being planar ultrasound images representing values along a second plane perpendicular to both (i) the raw ultrasound image, and (ii) the orientation of the thick-slice region corresponding to the thick-slice image being displayed. The orthogonal thin-slice images need to be reconstructed from the three-dimensional volumetric representation, as opposed to the raw ultrasound slices which can be taken directly from the raw data used to construct the three-dimensional volumetric representation. It is to be appreciated that while most examples of planar ultrasound images described herein are raw ultrasound slices or orthogonal thin-slice images, the scope of the preferred embodiments is not limited as such and extends to general cases of first and second planar ultrasound images having differing orientations.

Several features are provided on the adjunct display of FIG. 6 to assist the user in visualizing the location and orientation of the raw ultrasound slice 602 relative to the breast volume. First, an alphanumeric representation 603 of the actual raw slice number (in this example, slice number 300) out of the total number of raw slices (in this example, 533 slices) taken during the scanning process is shown. The three-dimensional icon 506 including the iconic rectangular solid 510 that roughly represents the breast volume outline is maintained in this view, with the position and orientation of the raw ultrasound slice 602 being shown therein by an iconic plane 604. In accordance with step 312 of FIG. 3, upper and lower range markers 606 and 608, respectively, indicate the upper and lower "y" for the thick-slice image 502 previously being viewed at a horizontal "z" position corresponding to the selected location 504 from FIG. 5. Depth range markers 612 indicate the vertical "y" extent for the thick-slice image 502 as well. Hash markers 610 also assist in locating the range markers 606 and 608. Finally, the location of range markers 606 and 608 relative to the raw ultrasound plane is also indicated by an iconic marker 605 on the three-dimensional icon 506.

In the example of FIG. 6, it is a raw ultrasound slice that is displayed because the ultrasound scans were taken directly in the y-z plane by the ultrasound scanning device 102 of FIG. 1. In a more general case, the raw ultrasound scans may not have been taken in planes perpendicular to the thick-slice region of the thick-slice image of FIG. 5. In those circumstances, a planar or thin-slice ultrasound image is reconstructed from the volumetric ultrasound data, the planar ultrasound image representing values along a plane perpendicular to the orientation of the relevant thick-slice region and passing through the second selected location of FIG. 5. The planar or thin-slice ultrasound image is preferably computed to represent as thin a slice as possible while remaining accurate, or to represent a slice having a thickness corresponding to the elevation beamwidth of the linear probe used to scan the breast if such type of probe was used.

At step 314 cine viewing of raw ultrasound or thin-slice image frames is accommodated, beginning at the frame of raw ultrasound slice 602. In the case of a mouse input, the cine can be controlled by a mouse wheel or mouse-mounted trackball. In the case of a touchscreen display, cine control can be achieved by a separate trackball provided near the display. A foot pedal can also be used for cine control to free up the hands of the user. Onscreen cine control buttons 614 can also be used.

At step 316 single-click or single-motion return to the selected enlarged inverted thick-slice image or to the array of inverted thick-slice images is accommodated. For example, a left-click of a mouse (or single-tap of a stylus on a touchscreen display) at a third selected location on the raw ultrasound slice 602 can bring up the enlarged thick-slice image corresponding to "y" depth of the third selected location, with a marker thereon indicating the (x,z) location of the third selected point. Alternatively, an onscreen "one slab" onscreen button 616 can be pressed to bring up the previous enlarged thick-slice image 502. A right click of a mouse (or double tap of a stylus on the touchscreen display) at the third selected point can bring up the array 402 of thick-slice images, with markers indicating the (x,z) position of the third selected location superimposed on the appropriate one of the thick-slice images for the "y" depth of the third selected location. Alternatively, an "all slab" onscreen button can be pressed to bring up the array 402 of thick-slice images.

Figure 7:
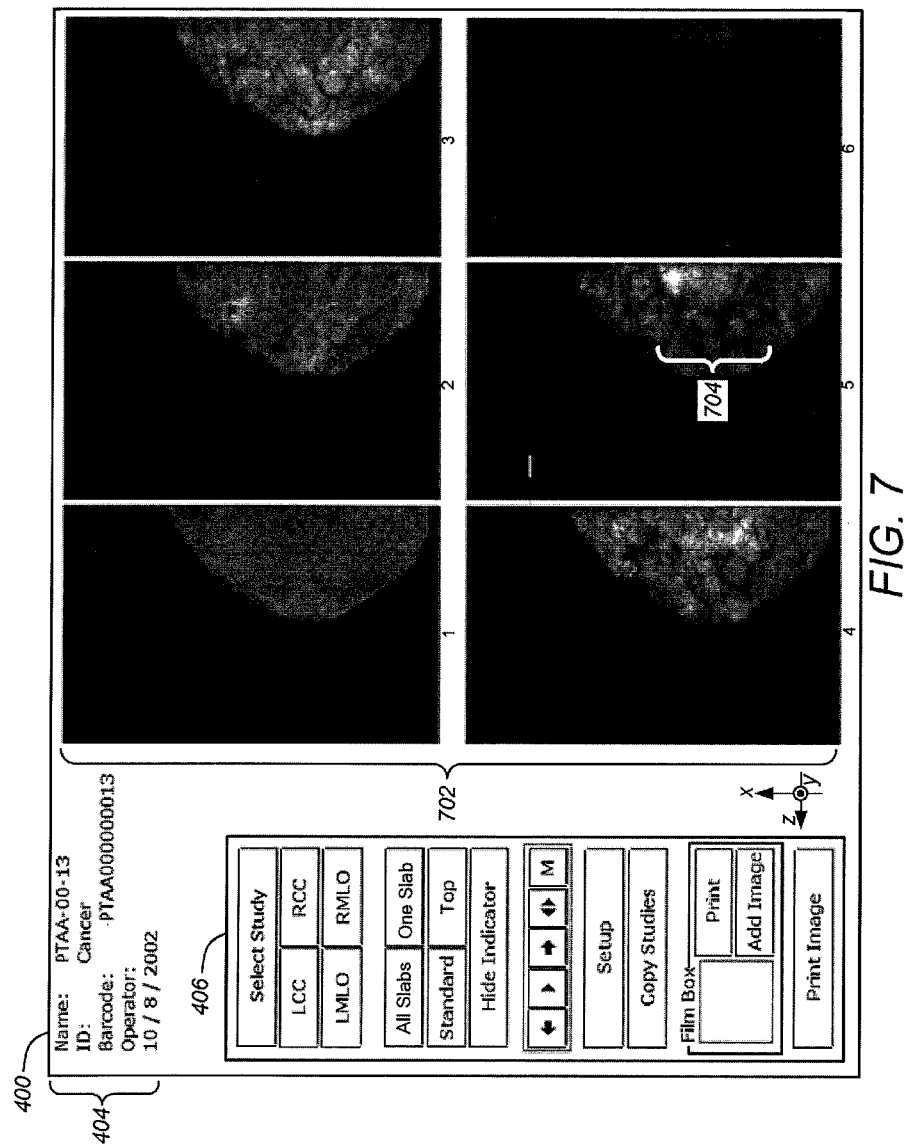
FIG. 7 illustrates an adjunct ultrasound display according to a preferred embodiment presenting an array of non-inverted thick-slice images for the same breast illustrated in FIG. 4.

FIG. 7 illustrates the adjunct ultrasound display screen 400 according to an alternative preferred embodiment in which an array 702 of non-inverted thick-slice images are displayed. The non-inverted thick-slice image array 702 corresponds to the same breast and ultrasound scanning session as for the inverted thick-slice image array of FIG. 4. With reference to a particular region 704 circled in FIG. 7, it has been found that the non-inverted thick-slice images 702 have a tendency to contain substantial areas of darkness in the breast tissue, wherein it is more difficult to detect subtle texture differences in breast tissue because it requires the differentiation of "dark" lesions from "less dark" or "differently dark" surrounding ligaments. This can lead to a larger number of false positives and also to user fatigue and frustration. In distinction, the inverted thick-slice images of FIG. 4 are easier to analyze, at least because of (i) the many years of training that most radiologists have in differentiating "bright" lesions from "bright" surrounding ligaments in x-ray mammograms, and (ii) the contrast enhancement performed at brighter output levels during the inversion step 214 supra.

FIG. 8 illustrates the adjunct ultrasound display 400 according to another preferred embodiment presenting an array 802 of thick-slice images that were inverted but for which the background segmentation and darkening steps were omitted. The thick-slice image array 802 corresponds to the same breast and ultrasound scanning session as for the thick-slice image arrays of FIG. 4 and FIG. 7. As indicated in FIG. 8, the outlying non-breast areas are bright instead of dark. In addition to being less familiar to most radiologists trained on x-ray mammograms, it is believed that this preferred embodiment might also lead to greater eyestrain. However, this preferred embodiment might nevertheless represent a desirable display format for some nonzero population of users.

Figure 9:
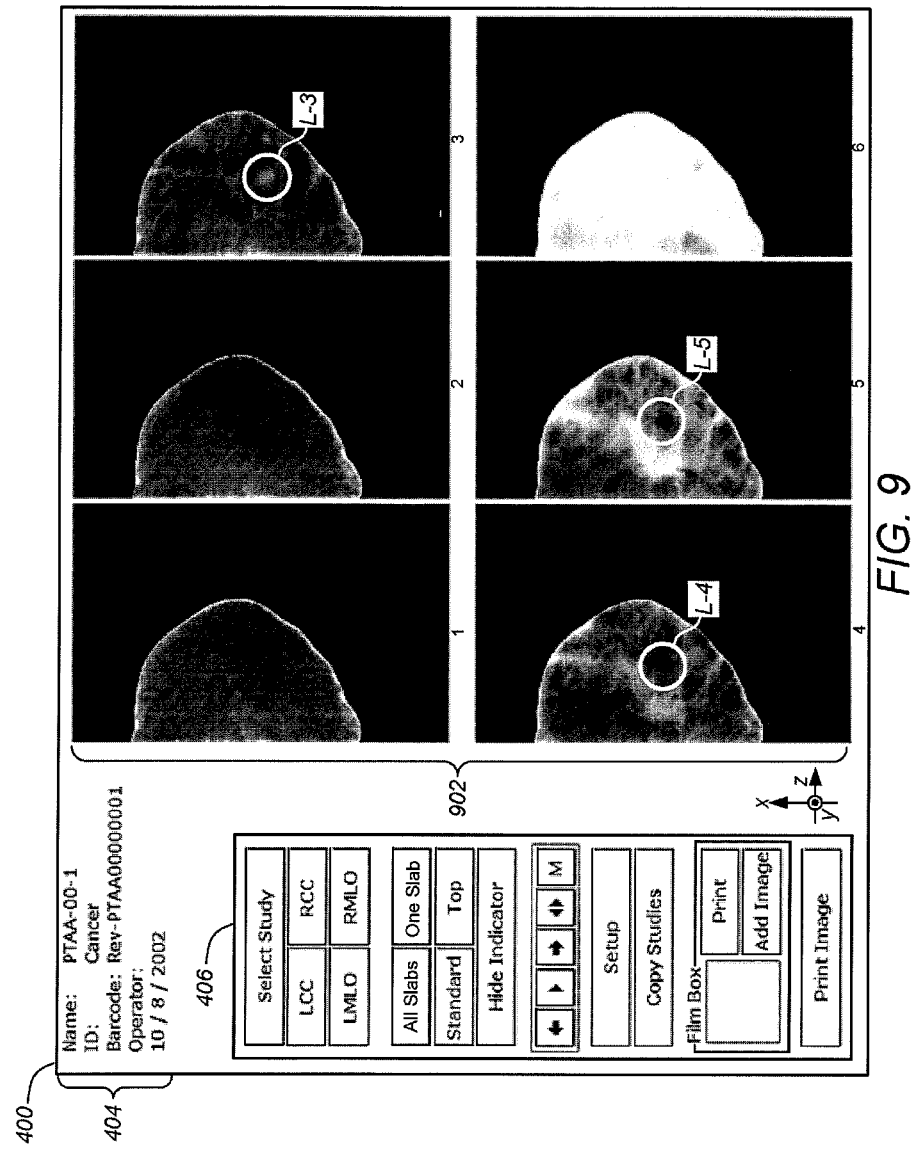
FIG. 9 illustrates an adjunct ultrasound display according to a preferred embodiment presenting an array of inverted thick-slice images.
Figure 10:
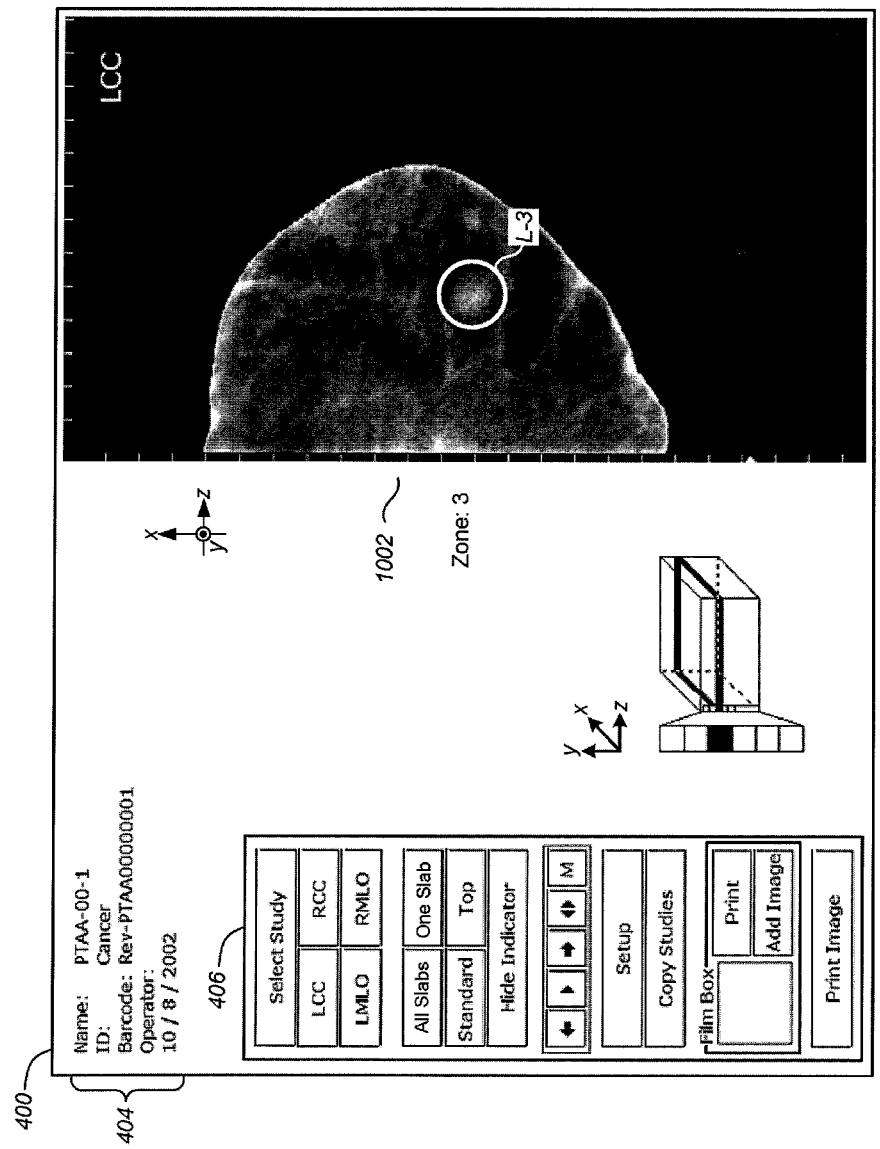
FIG. 10 illustrates an adjunct ultrasound display according to a preferred embodiment presenting an enlarged inverted thick-slice image.

FIGS. 9-11 illustrate a thick-slice image array 902, an enlarged thick-slice image 1002, and a raw ultrasound slice 1102, respectively, in a manner analogous to the images 402, 502, and 602 of FIGS. 4-6, but for a different patient. FIGS. 9-11 illustrate one of the many features and advantages of the preferred embodiments wherein in which lesion shadows among successive thick-slice images, or the lack thereof, can rapidly assist in a diagnosis. Circled in FIG. 9 are locations L-3, L-4, and L-5 to indicate a particular (x,z) location L at thick-slice zones 3, 4, and 5, respectively. Notably, there is a white spot in the third zone at L-3, as illustrated on both FIG. 9 and FIG. 10, but there are dark spots in corresponding areas L-4 and L-5 of the fourth and fifth zones lying underneath the third zone. This indicates that there were low acoustic reflection readings for the third zone at L-3, while there were high acoustic reflection readings for two zones directly therebelow at L-4 and L-5. Accordingly, it is highly likely that this is a benign liquid-filled cyst that can be readily ignored. This can be quickly verified by viewing the raw ultrasound slice 1102 of FIG. 11, which shows a dark area 1104 of low reflections over an area 1106 of accentuated reflections.

Thus, according to a preferred embodiment, a method for quickly diagnosing the presence of a benign, liquid-filled cyst is provided, comprising the step of viewing an array of inverted thick-slice ultrasound images including a first inverted thick-slice image and a plurality of neighboring inverted thick-slice images, the neighboring inverted thick-slice images corresponding to thick-slice regions directly below the thick-slice region of the first inverted thick-slice image relative to an ultrasound detector. The method further comprises the steps of observing a bright spot in the first thick-slice image and searching for dark spots in the plurality of neighboring inverted thick-slice images at locations corresponding to the bright spot. If such dark spots are present, the bright spot of the first inverted thick-slice image is diagnosed to be a benign, liquid-filled cyst. The method further comprises the step of verifying such diagnosis by viewing a raw ultrasound slice or reconstructed thin-slice image having a plane that passes through the breast location indicated by the bright.

With reference to FIG. 11, selected onscreen control buttons 406 are now described. An onscreen "select study" onscreen button 1150 activates a file selection dialog box in which the user can select adjunctive ultrasound data for a particular patient and scan session. Onscreen "view selection" buttons 1152 select the desired view of LCC, RCC, LMLO, and RMLO. Onscreen display selection buttons 1154 allow the user to select the "all slab" view of FIG. 4, the "one slab" view of FIG. 5, the "standard" view of FIG. 6, or a "top" view representing an integration of all thick-slice regions for that view. Onscreen "film box" buttons 1156 allow for easy collection and/or printing of interesting images for subsequent review.

Figure 12A:
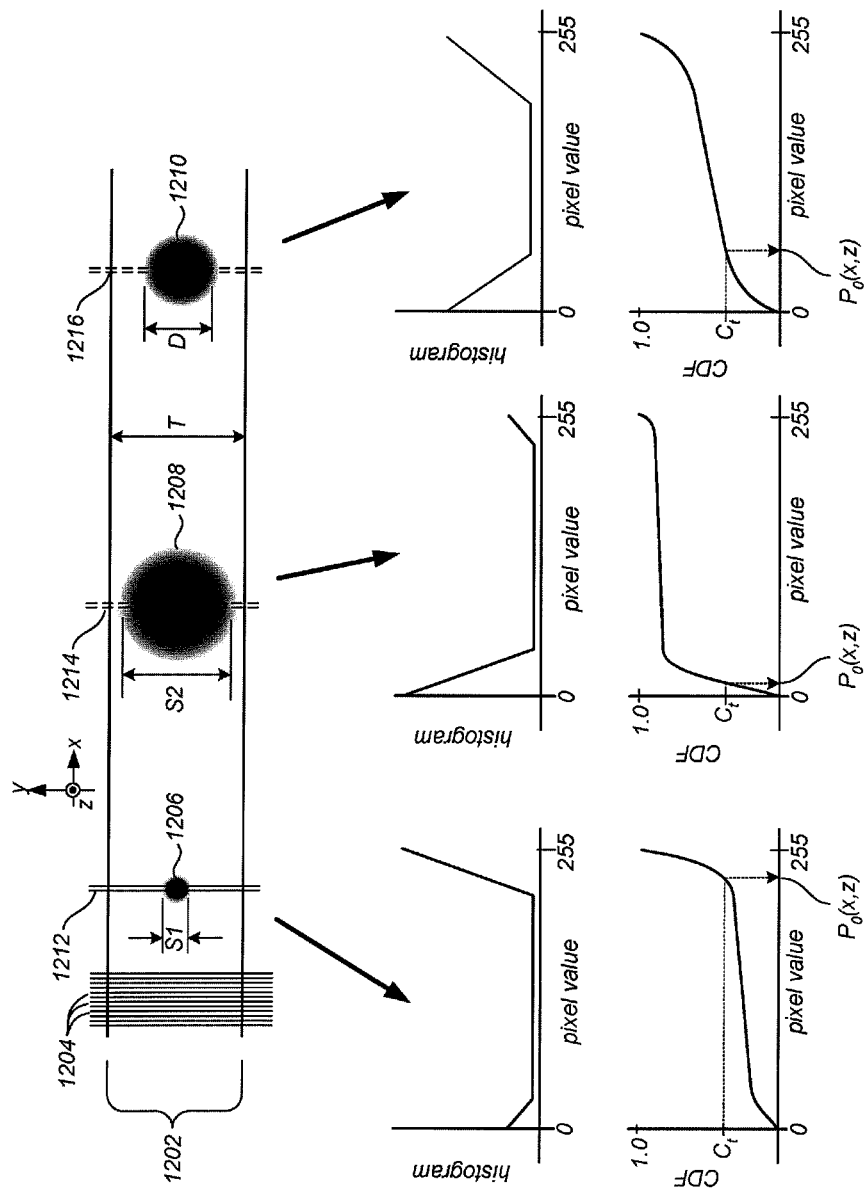
FIG. 12A illustrates a conceptual view of a thick-slice region and lesions contained therein, along with related histograms and cumulative distribution functions.

FIG. 12A illustrates a conceptual view of a thick-slice or slab-like region 1202 substantially parallel to the CC plane, along with hypothetical mass lesions 1206, 1208, and 1210, presented for describing thick-slice image computation according to a preferred embodiment. As indicated by the provided reference axes, the thick-slice region 1202 is being viewed from the +z direction, i.e., from the front of the woman. The thick-slice region 1202 has a thickness T which can be about 1 cm for this example. The described thick-slice image computation algorithms operate on standard, non-inverted ultrasound voxel values for which zero is "dark" and 255 is "bright," although it is to be appreciated that it could be readily adapted by a person skilled in the art in view of the instant disclosure to operate on inverted ultrasound voxel values or otherwise-remapped voxel values.

Shown in FIG. 12A are side views of pixel columns 1204, including pixel columns 1212, 1214, and 1216 passing through the hypothetical mass lesions 1206, 1208, and 1210, respectively. A given pixel column extending downward in the y direction passing through the thick-slice region at pixel location (x,z) could comprise, for example, 40-60 voxels, each having an 8-bit value $V_{xz}(y_n)$. For each pixel column passing through the thick-slice region 1202, a scalar output value $P_0(x,z)$ is computed that constitutes the thick-slice image at that pixel location. In a simplest preferred embodiment, the thick-slice computation algorithm simply computes an average pixel value, as described by Eq. (2) below, where N is the number of voxels in the pixel column at (x,z):

$$P_0(x, z) = \frac{\sum_{n=1}^{N} V_{xz}(y_n)}{N} \quad (2)$$

However, it has been found that thick-slice images more useful in breast cancer screening can be achieved by using a thick-slice computation algorithm that detects particular statistical variations of $V_{xz}(y_n)$ in the neighborhood of masses in a manner that emphasizes masses larger than a predetermined target size and de-emphasizes smaller masses in the in the resulting thick-slice image.

Shown in FIG. 12A for each of the pixel columns 1206, 1208, and 1210 passing through the respective hypothetical mass lesions is a histogram of the number of pixel elements at each respective gray value. Under the non-inverted convention of FIG. 12, the mass lesions of interest for breast cancer screening purposes tend to show up as "dark" regions against "whiter" backgrounds. It is to be observed that pixel columns passing through smaller masses, such as pixel column 1212 passing through mass 1206 having size S1, have substantially more high pixel values than low pixel values, as revealed by the associated histogram curve. As such, the area under the histogram from zero to a pixel value, termed herein the CDF or cumulative distribution function of $V_{xz}(y_n)$, remains low for most pixel values and only increases as higher pixel values are reached. Conversely, pixel columns passing through larger masses, such as pixel column 1214 passing through mass 1208 of size S2, have substantially more low pixel values than high pixel values, as revealed by the associated histogram curve and CDF.

According to a preferred embodiment, a target size D is established representing a mass size expected to be interesting from a breast cancer screening point of view. For purposes of this example, and not by way of limitation, a suitable target size D can be about 0.5 cm, which yields a target size to slab thickness ratio (D/T) equal to 0.5. The output pixel value $P_0(x,z)$ is set equal to that pixel value for which the cumulative distribution function of $V_{xz}(y_n)$ is equal to a preselected value K times the target size to slab thickness ratio. This is graphically illustrated in FIG. 12 and expressed in Eq. (3) below:

$$CDF_{V_{xz}}[P_0(x, z)] = K\left(\frac{D}{T}\right) \quad (3)$$

Figure 12B:
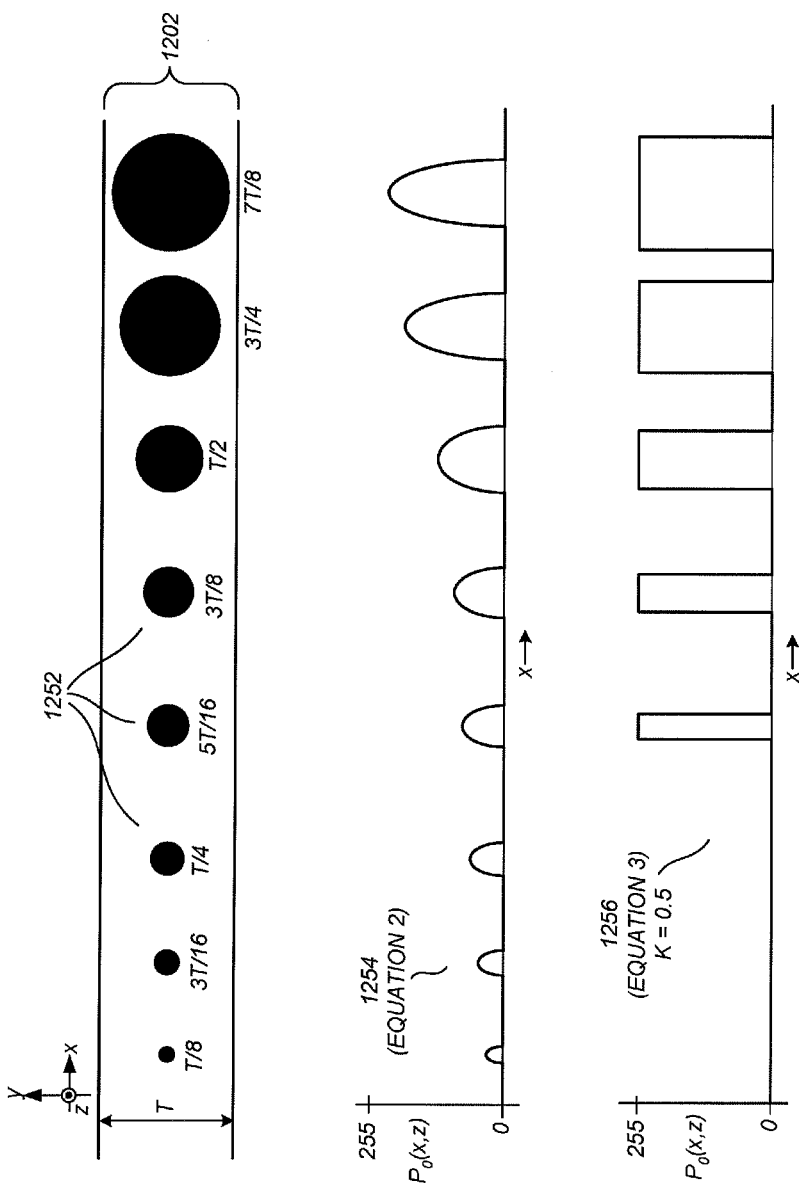
FIG. 12 B illustrates a conceptual view of a thick-slice region and lesions contained therein, along with plots of thick-slice image values along a single line in the thick-slice image resulting from thick-slice image computation algorithms according to preferred embodiments.

FIG. 12B illustrates a conceptual view of the thick-slice region 1202 and lesions 1252 contained therein for a single fixed value of $z=z_{fixed}$, along with plots 1254 and 1256 of thick-slice image values $P0(x, z_{fixed})$ along a single line, the thick-slice images being computed according to Eqs. (2) and (3), respectively. For ease of computation and presentation, the lesions and surrounding breast tissue are assigned the extreme brightness values of 0 and 255, respectively. Although this conceptualizes the example somewhat by using an "extremely" bimodal voxel value distribution, it is to be appreciated that regions near mass lesions often have histogram distributions with a roughly bimodal characteristics, and so the results of FIG. 12B are roughly representative of the actual results obtained. A preselected value of K=0.5 was used in the application of Eq. (3). As indicated by a comparison of plot 1254 versus the plot 1256, the use of the CDF-based method of Eq. (3) yields a resulting thick-slice image that enhances the visibility of lesions as they approach and exceed the target size D, while de-emphasizing smaller lesions. Different values of K may be used in Eq. (3), e.g., in the range of 0.25 to 0.75, and the value may be optimized for a given configuration based on empirical results. Generally speaking, as K is increased there is decreased "sensitivity" with more of the smaller lesions being ignored. In an alternative preferred embodiment, the value of K may be dynamically assigned based on local volume characteristics, for example, as a function of the local statistical variance of the voxel values.

Figure 13:
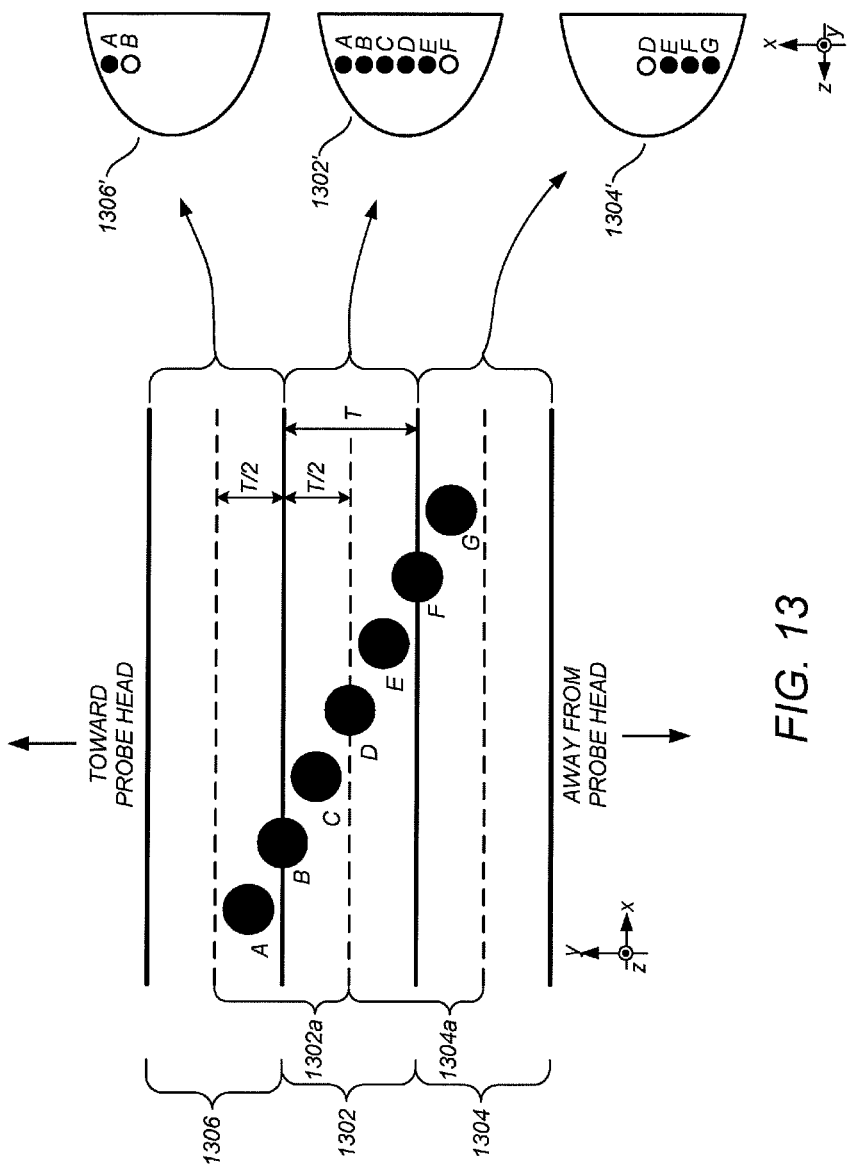
FIG. 13 illustrates a conceptual frontal view of a set of neighboring thick-slice region and lesions contained therein, along with conceptual thick-slice images.

FIG. 13 illustrates a border compensation method for thick-slice generation according to the preferred embodiments that compensates for the possibility that lesions may straddle thick-slice borders. Shown in FIG. 13 is an exemplary thick-slice region 1302 vertically adjacent to an upper thick-slice region 1306 and a lower thick-slice region 1304. Also shown in FIG. 13 are exemplary mass lesions A-G, some of which are entirely contained in one of the thick-slice regions and some of which straddle the thick-slice region borders. As indicated in FIG. 13, the terms upper and lower are indicative of a distance from an ultrasound probe used to scan the breast volume. According to a preferred embodiment, when computing a thick-slice image, two alternative thick-slice values for each location (x,y) are computed, including a first value corresponding to the actual borders of the thick-slice region and a hypothetical value corresponding to the borders of a hypothetical thick-slice region having a similar thickness but extending into the next upper thick-slice region. In the example of FIG. 13, a hypothetical thick-slice regions 1302a and 1304a correspond to thick-slice regions 1302 and 1304, respectively. For each location (x,z) in the thick-slice image, the lesser (i.e., "darker") of the first value and the hypothetical value is used.

Also shown in FIG. 13 are conceptual thick-slice images 1302', 1304', and 1306' corresponding to thick-slice regions 1302, 1304, and 1306, respectively. In this example, it is presumed that there are no lesions in the breast other than the mass lesions A-G. For purposes of presentation, a filled-in circle is shown when the "entire effect" of a mass lesion is present in the thick-slice image, whereas an empty circle is shown when only a "half effect" is present. Notably, whereas the lesion B would only be "half-present" in both of the thick-slice images 1306' and 1302' in an uncompensated scenario (not shown), it is "fully-present" in the thick-slice image 1302' as well as "half present" in thick-slice image 1306' in the compensated scenario shown in FIG. 13. Lesion A, which would be fully-present in thick-slice image 1306' and not present in thick-slice image 1302' in an uncompensated scenario, is fully-present in both of the thick-slice images 1306' and 1302' in the compensated scenario. It has been found that this border-straddling compensation strategy, for which other examples are presented in FIG. 13, represents a desirable result even though it tends to "redundantly" show the same lesion twice. It has been found that it is more desirable to provide "redundant" showings of the same mass lesion in two adjacent thick-slice images than to fail to display the "full effect" of a mass lesion straddling the borders of those slices. Also, because the display of the ultrasound thick-slices is only used in an adjunctive diagnostic sense, and not in an absolute diagnostic sense, there are few if any practical implications for overall system specificity.

Figure 14:
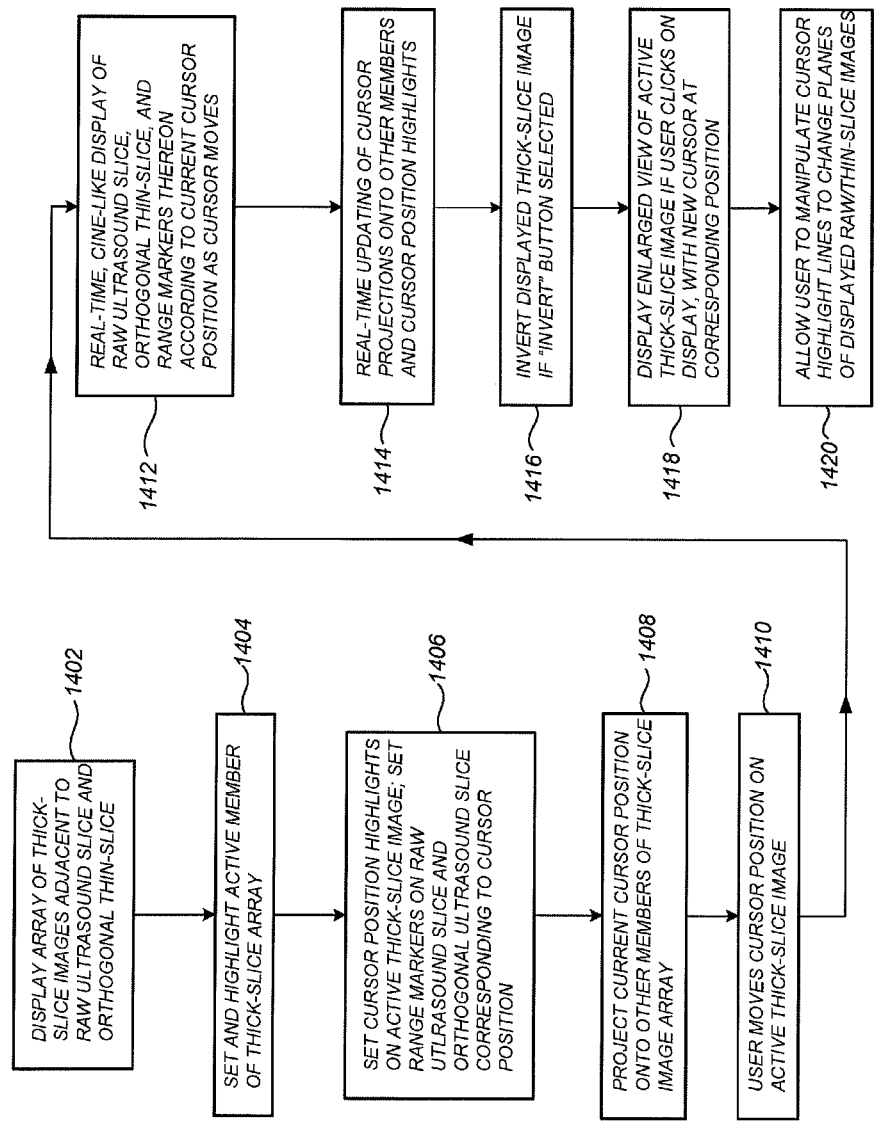
FIG. 14 illustrates steps for interactively displaying adjunctive ultrasound mammography information to a user according to a preferred embodiment.

FIG. 14 illustrates steps for interactive display of adjunctive ultrasound mammography information according to a preferred embodiment. The steps of FIG. 14 are further illustrated in the adjunct displays of FIGS. 15-17. At step 1402, an array of thick-slice images is displayed adjacent to a raw ultrasound slice and an orthogonal thin-slice image. With respect to FIG. 15, the array of thick-slice images 1502 is displayed next to planar ultrasound images 1504 including a raw ultrasound image 1506 and an orthogonal thin-slice image 1508. At step 1404, an active member of the thick-slice array is selected, such as by receiving a simple mouse point-and-click from the user, and is then highlighted. With respect to FIG. 15, thick-slice array 1502 comprises an active member 1510 having a highlighted marking 1519 shown thereon. First and second range markers 1513 and 1514, respectively, are provided on the raw ultrasound image 1506 and the orthogonal thin-slice image 1508, respectively, marking the upper and lower border of the thick-slice region of the active slice 1510 at a horizontal position corresponding to a cursor marker 1512 thereon.

Superimposed on active member 1510 are first and second plane indicators 1517 and 1518, respectively. The first plane indicator 1517 corresponds to a first plane through the breast volume as displayed by the raw ultrasound image 1506, and is visually related thereto by means of a color such as green that matches colored lines at the edges of the raw ultrasound image 1506. Preferably, the colored lines at the edges of raw ultrasound image 1506 extend from the posterior edge thereof across to the current position of the range marker 1513, which makes it easier to keep track of the first range marker 1513 as the cursor 1512 is moved by the user. The plane indicator 1517 is likewise heavily drawn from the posterior edge to the cursor position and then lightly drawn over to the anterior edge to assist tracking. According to an alternative preferred embodiment, the first range marker 1513 can remain fixed at the center of the frame, while the rest of the raw ultrasound slice dynamically shifts around it according to user cursor movements. Similar descriptions apply to second plane indicator 1518, orthogonal thin-slice image 1508, and second range marker 1514.

At step 1408 the position of cursor 1512 on active member 1510 is projected onto other members of the thick-slice image array. Shown in FIG. to 15 with respect to a representative second member image 1515 is a projected cursor 1516. Also shown in the second member image 1515 are projected first and second plane indicators 1517a and 1518a.

Figure 16:
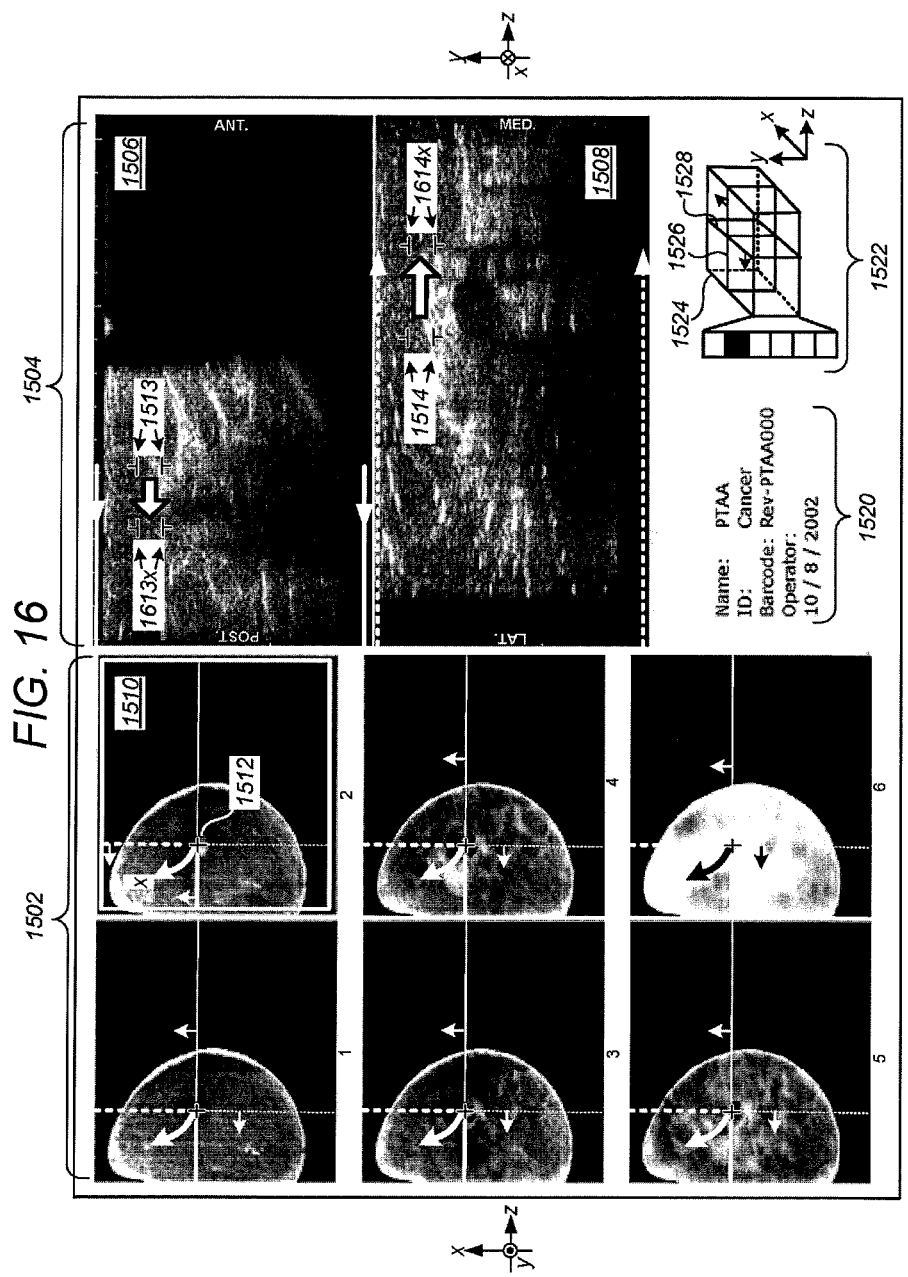
FIG. 16 illustrates the adjunct ultrasound display of FIG. 15 when a user moves the cursor on a selected thick-slice image.

At step 1410 the user moves the cursor position on the active thick-slice image. At step 1412 in a real-time "cine-like" display is provided wherein the planar images 1504 are refreshed in real-time to keep up with the current position of plane indicators 1517 and 1518, which follow the cursor position. At step 1414, real-time updating of the cursor projections and the plane indicator projections is provided. According to a preferred embodiment, shifts in the position of cursor 1512 and corresponding shifts in the plane indicators 1517 and 1518 are mirrored in the other members of the thick-slice array, as illustrated in FIG. 16. FIG. 16 also shows how range markers 1513 and 1514 are shifted to new positions 1613x and 1614x, respectively, during the cursor shift, as well as the manner in which the colored edges of the planar images shift with cursor position.

Figure 15:
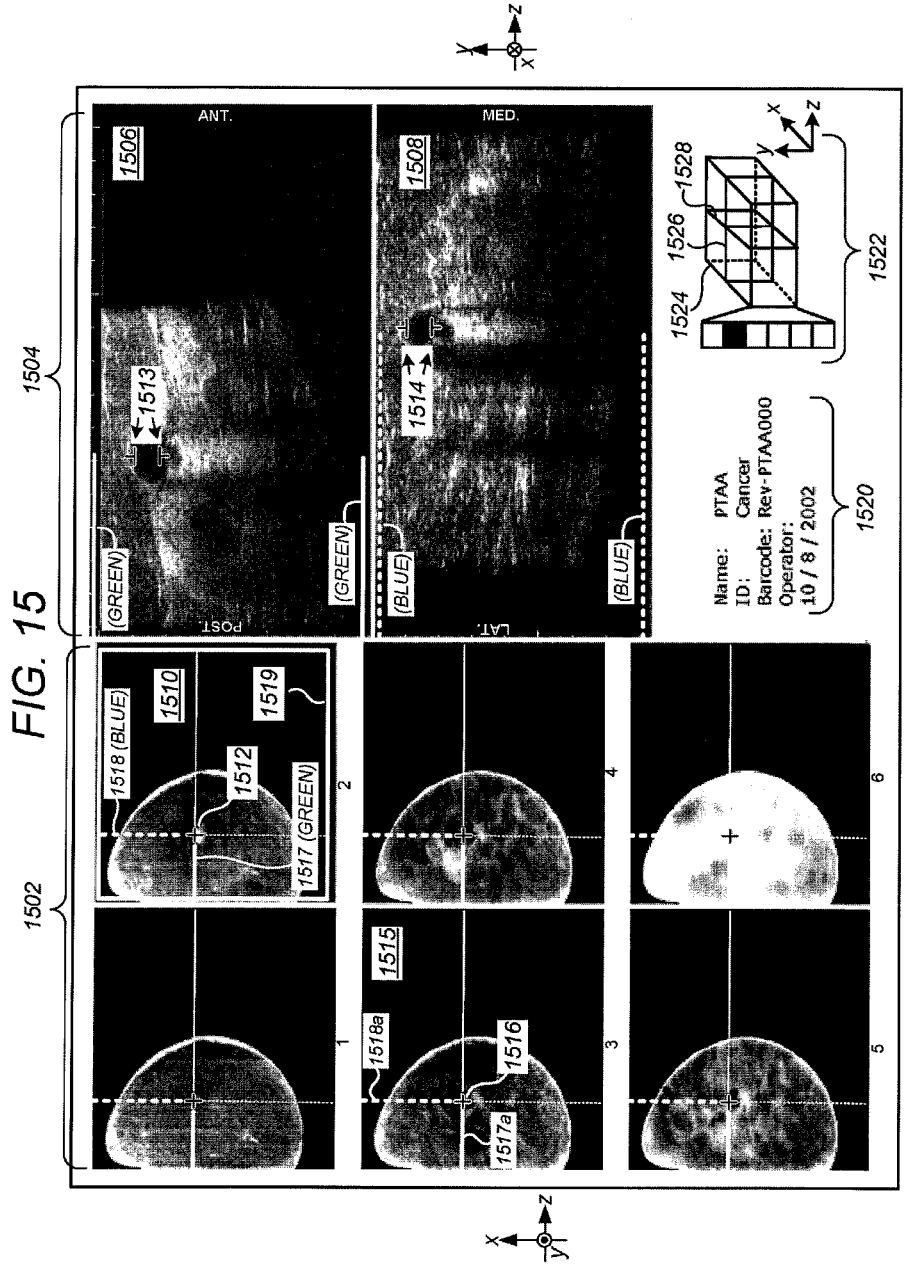
FIG. 15 illustrates an adjunct ultrasound display according to a preferred embodiment presenting an array of inverted thick-slice images and two planar ultrasound images.

Also shown in FIGS. 15 and 16 is a patient ID 1520 and a three-dimensional icon 1522. The three-dimensional icon 1522 comprises a frame structure 1524 similar to the frame structure 510 of FIG. 5, and two iconic plane indicators 1526 and 1528 thereon corresponding to plane indicators 1517 and 1518, respectively. As indicated in FIG. 16, the iconic plane indicators 1526 and 1528 also move dynamically with the cursor position.

In one preferred embodiment, the look and feel of the cursor movement is analogous to a computer-aided drawing display (e.g., Microsoft Visio) in which the cursor can, at the user's option, "stick" to horizontal and vertical "grid lines". This allows for one of the planar ultrasound images 1506 or 1508 to remain perfectly static if the cursor is moved along the horizontal or the vertical directions. As described supra, in an alternative preferred embodiment the range markers 1513 and 1514 can remain fixed at the center of the planar ultrasound frame, while the images move around them, it being found that many users can focus better on the tissue near the cursor position using this method.

In the display of FIGS. 15-16, soft buttons analogous to those of FIGS. 4-11 are omitted in favor of a mechanical keypad described infra, although the scope of the preferred embodiments is by no means so limited. At step 1416, the displayed thick-slice images are inverted (see FIG. 8, supra) when the user presses an "invert" button on the keypad. Preferably, when an inverted convention is used, the background is segmented out and returned to dark. At step 1418 an enlarged view of the active thick-slice image is displayed if the user clicks or taps on a selected cursor position or enters a "one slab" keypad entry.

Figure 17:
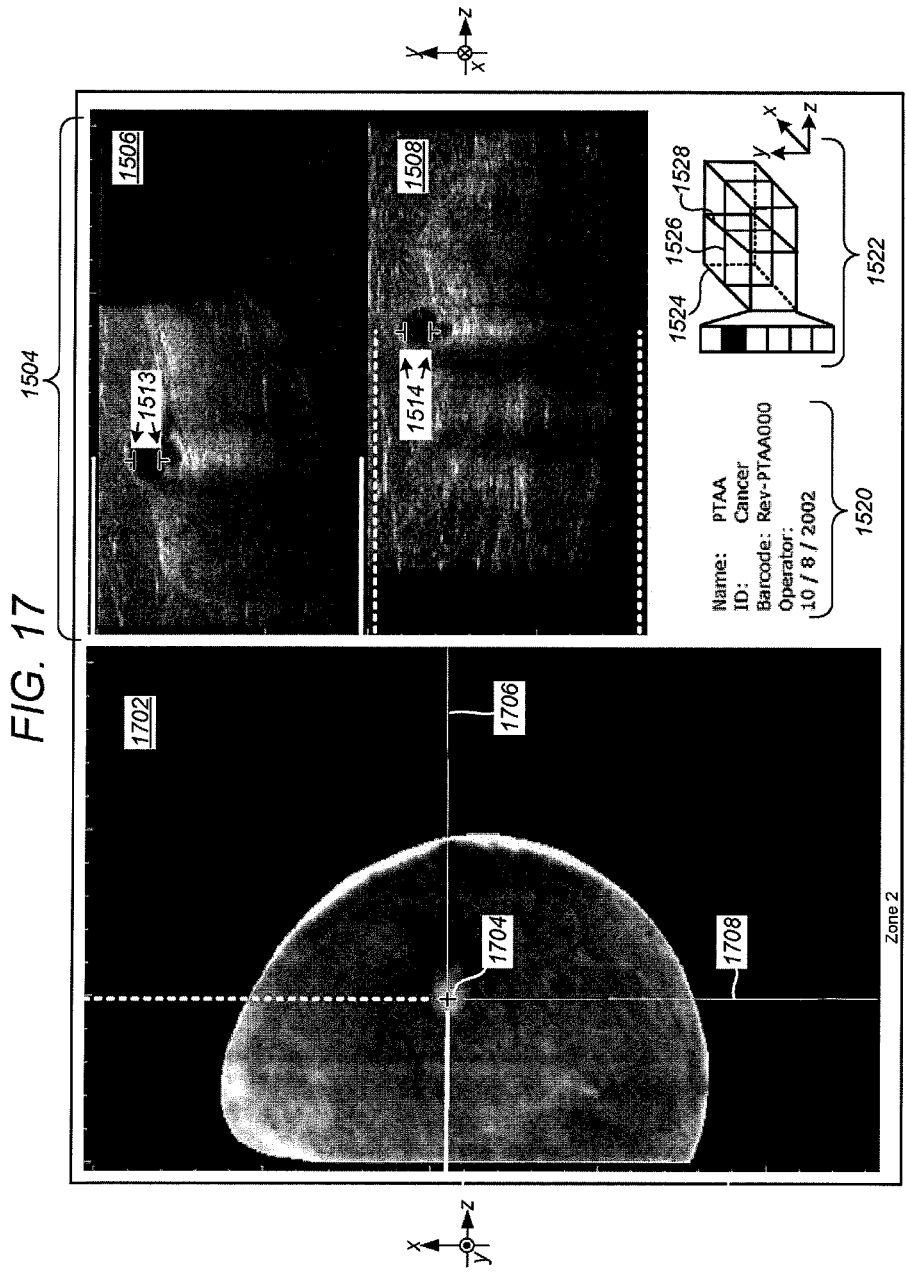
FIG. 17 illustrates an adjunct ultrasound display according to a preferred embodiment comprising an enlarged inverted thick-slice image and two planar ultrasound images.

FIG. 17 illustrates an enlarged view 1702 of the active thick-slice image member 1510 of FIGS. 15-16 that appears at step 1418. The cursor position 1704 corresponds to the same breast location as the selected cursor position 1512 of FIG. 15. At step 1420, the user is permitted (on either the one-slab or all-slab displays) to manipulate the orientation and positions of plane indicators 1706/1708 or 1517/1518 in a manner similar to the way a computer draftsperson manipulates lines in a graphical illustration, while in real-time the planar ultrasound images 1504 remain updated to reflect corresponding planes through the breast volume.

Figure 18:
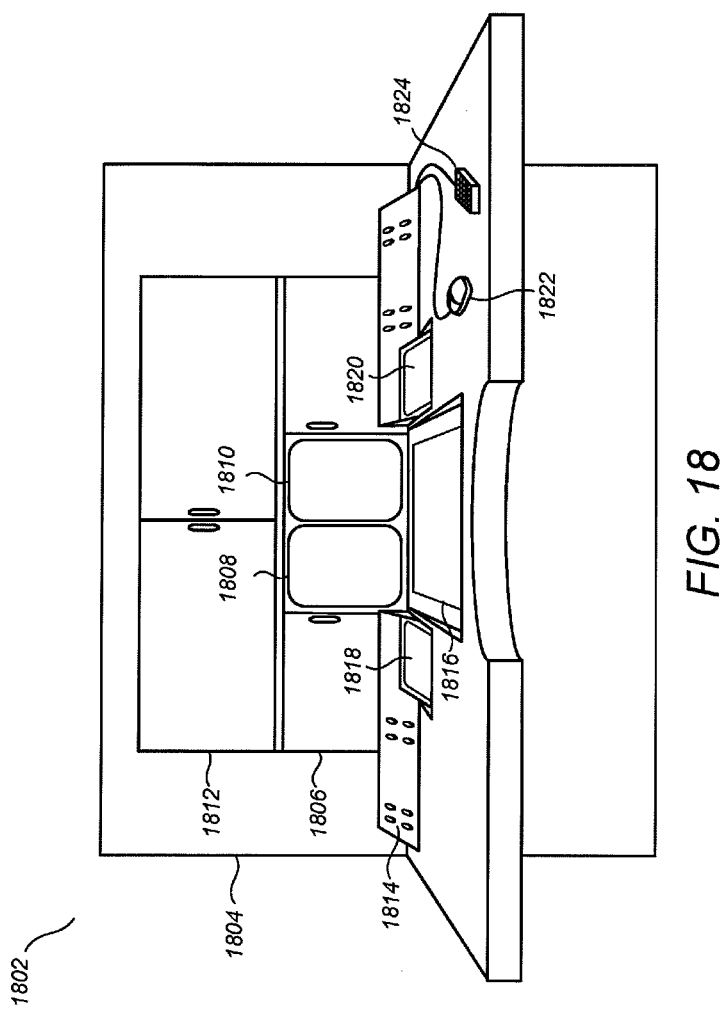
FIG. 18 illustrates an exterior view of an adjunctive ultrasound mammography display unit according to a preferred embodiment.

FIG. 18 illustrates an exterior view of an adjunctive ultrasound mammography display unit 1802 in accordance with a preferred embodiment. Adjunctive ultrasound mammography display unit 1802 comprises an x-ray film conveyor and display unit 1804 with modifications made to accommodate adjunctive ultrasound display. X-ray film conveyor and display unit 1804 comprises a lower film conveyor 1806 and an upper film conveyor 1812, the lower conveyor 1812 being turned off in this example and the lower conveyor 1806 displaying two x-ray mammogram images 1808 and 1810. Conventional control buttons 1814 provided with most commercially available x-ray film conveyor and display units are provided to control the x-ray mammogram film conveyors.

According to a preferred embodiment, adjunctive ultrasound mammography display unit 1802 comprises a full-sized LCD display 1816 integrated into a front table portion thereof as shown in FIG. 18. Preferably, LCD display 1816 is large enough to display two full-scale thick-slice ultrasound images simultaneously, including a left image corresponding to the x-ray mammogram image 1808 and a right image corresponding to x-ray mammogram image 1810. A 17-inch diagonal LCD display has been found suitable to achieve this objective. In contrast to the preferred embodiment of FIG. 1, supra, LCD display 1816 is conveniently located to allow back-and-forth viewing between the thick-slice images and the x-ray images in an up-and-down manner, with minimal head motion. As discussed previously, even subtle ergonomic issues can be of crucial importance in the breast cancer screening process, because if the image viewing apparatus leads to tired or physically fatigue radiologists, such fatigue can unfortunately transform into a potentially fatal missed diagnosis or, alternatively, the inefficient process of an unnecessary patient callback.

In distinction contrast to cathode ray tube (CRT) monitors of equivalent viewable size, the LCD display 1816 can be advantageously placed in the middle of the table portion without interfering with the knees of the user. Adjunctive ultrasound mammography display unit 1802 further comprises CRT monitors 1818 and 1820 directly to the left and right of the LCD display 1816, respectively. Preferably, the CRTs have a 7-inch diagonal screen. It has been found more desirable to present the above planar ultrasound images (e.g., raw ultrasound slices and orthogonal thin-slice views) on smaller CRT displays on the side of a larger LCD thick-slice display. The smaller CRT display allows for a substantially increased brightness range and also represents a more familiar optical characteristic to users familiar with traditional ultrasound displays. Among these characteristics is a slight low-pass filtering effect due to the finite width of the cathode-ray beam, in distinction to a pixellating effect that can be observed on LCD monitors. Because the CRT monitors 1818 and 1820 are set back and to the side of the LCD monitor 1816, they do not interfere with the knees of the user. Adjunctive ultrasound mammography display unit 1802 further comprises a mouse 1822 and a keypad 1824 for controlling the adjunctive ultrasound mammography displays.

Figure 19:
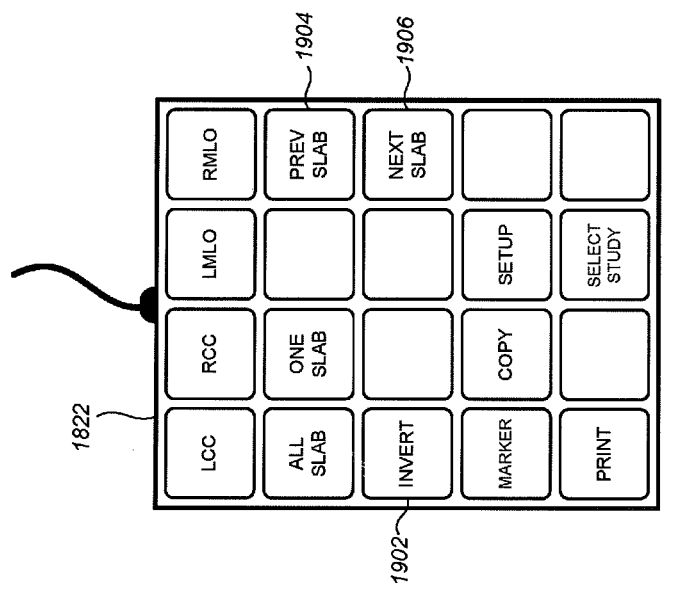
FIG. 19 illustrates a keypad for the adjunctive ultrasound mammography display unit of FIG. 18.

FIG. 19 illustrates the keypad 1822 of FIG. 18 in more detail. The keypad 1822 provides functionality similar to the soft buttons described supra with respect to FIG. 11, with some additional capabilities relevant to the preferred embodiments of FIGS. 15-17. An "invert" key 1902 causes the display of all thick-slice images to be inverted, as described supra with respect to FIG. 14. Also, a "prey slab" key 1904 and "next slab" key 1906 are provided as an additional method for allowing the user to change the active member of the thick-slice array being displayed.

Figure 20:
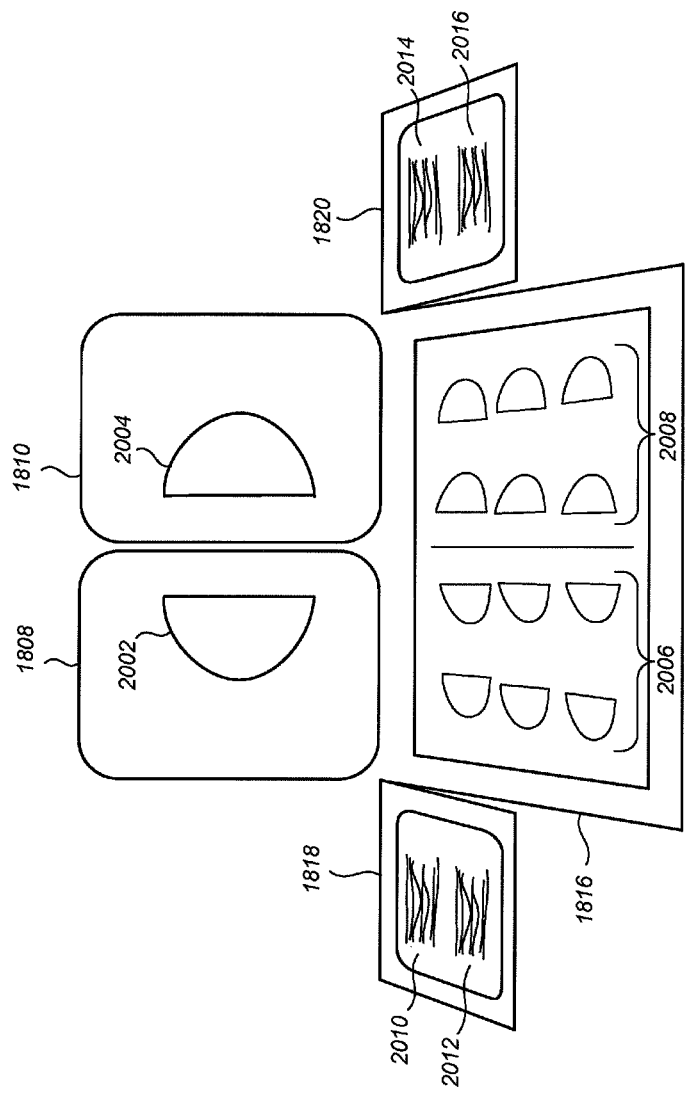
FIG. 20 illustrates a closer view of display portions of the adjunctive ultrasound mammography display unit of FIG. 18.

FIG. 20 illustrates an x-ray/adjunctive ultrasound mammography display according to a preferred embodiment as implemented on the apparatus of FIG. 18. An example is shown for the CC view, it being understood that an equivalent display is also provided for the MLO view. The MLO x-ray views may be shown, for example, on the upper conveyor 1812 of FIG. 18, while a toggle button allows the corresponding adjunctive ultrasound images for the MLO view to be displayed on monitors 1816, 1818, and 1820. Shown in FIG. 20 is an RCC x-ray mammogram film 2002 and an LCC x-ray mammogram film 2004. On the left hand side of LCD display 1816 is a thick-slice array 2006 for the CC view of the right breast, and on the right hand side of LCD display 1816 a thick-slice array 2008 for the CC view of the left breast. CRT monitor 1818 displays a raw ultrasound image 2010 and orthogonal thin-slice view 2012 corresponding to a current active cursor position on the RCC thick-slice display 2006. CRT monitor 1820 shows equivalent planar ultrasound images 2014 and 2016 for the LCC thick-slice display 2008.

According to an alternative preferred embodiment, only a single CRT display is provided to one side of the central LCD display, the central LCD display showing thick-slice images for only a single breast, and the CRT display showing the corresponding planar ultrasound images. This alternative preferred embodiment can be advantageous for cost and space considerations, as well as in recognition of the fact that the user will generally only be closely analyzing a single breast of a time.

According to another alternative preferred embodiment, one side of FIG. 20 displays CC views (CC x-ray, CC thick-slice images, and CC planar ultrasound images) for a single breast, while the other side of FIG. 20 displays MLO views (MLO x-ray, MLO thick-slice images, and MLO planar ultrasound images) for that breast. This preferred embodiment can be advantageous insofar as all standard information for the breast is now provided in a single set of images being concurrently displayed, rather than requiring the user to physically instantiate switches between CC and MLO views of the same breast during analysis.

A variety of other configurations, each having its particular advantages, is also within the scope of the preferred embodiments. By way of example, the thick-slice images may instead be provided on paper or on film, while the electronic display of thin-slice images are an optional addition to the unit. Where the thick-slice images are provided on film, a technician can simply load the thick-slice image films into the conveyor unit adjacent to or above the standard x-ray films.

According to another preferred embodiment relating generally to the method of FIG. 14, the user may instantiate a cine display for the raw ultrasound image 1506, the orthogonal thin-slice image 1508, or a combination of both along a predetermined cursor trajectory. By way of example, responsive the user pressing an additional button "lat-med cine" (not shown) on keypad 1822, a cine display of the raw ultrasound slice 1506 is displayed with the cursor 1512/1704 moving automatically in a vertical direction on thick-slice image 1510/1702 at its current horizontal position. The orthogonal thin-slice image 1508 will remain static. The user can control the cine display using additional cine control buttons (not shown) on keypad 1822. Likewise, responsive the user pressing an additional button "post-ant cine" (not shown) on keypad 1822, a cine display of the orthogonal thin-slice image 1508 is displayed with the cursor 1512/1704 moving automatically in a horizontal direction on thick-slice image 1510/1702 at its current vertical position, the raw ultrasound image 1506 remaining static. It is preferable that this preferred embodiment be used in conjunction with the particular above-described preferred embodiment in which the range markers 1513 and 1514 are fixed at the center of the frame.

In a slightly more complicated preferred embodiment, controls are provided for which the user can select a custom cine trajectory, wherein both of the planar ultrasound images 1506 and 1508 will change as the cursor 1512/1704 automatically follows that trajectory. The user can select the custom cine trajectory, for example, by manipulating the plane indicators 1517/1518 in a Visio-like manner as described previously. The user can then activate the cine action by pressing the "lat-med" cine button to make the cursor 1512/1704 move along the plane indicator 1518, or by pressing the "lat-med" cine button to make the cursor 1512/1704 move along the plane indicator 1517.

According to another preferred embodiment, CAD markers identifying suspicious lesions are superimposed on the thick-slice images 1502 to direct the attention of the user to those particular locations. Preferably, the CAD markers are generated from the volumetric ultrasound scan data used to generate the displayed thick-slice images 1502, although the scope of the preferred embodiments is not so limited. According to a preferred embodiment, the CAD markers are displayed responsive to the user pressing a "show CAD marker" button (not shown) on keypad 1822, and are superimposed on the currently-showing thick-slice display, i.e. the thick-slice array 1502 or the enlarged thick-slice image 1702. The CAD markers may be color-coded, size-coded, shape-coded, mode-coded (blinking, flashing, etc.), etc., and/or accompanied by nearby alphanumeric tags or text messages to conveniently portray higher-suspiciousness lesions versus lower-suspiciousness lesions. Preferably, where the user presses the "show CAD marker" button as the thick-slice array 1502 is displayed, the active thick-slice image is automatically selected to be that member containing the most-suspicious lesion, the cursor 1512 is automatically relocated to the location of that lesion, and the planar ultrasound images 1506 and 1508 thereby automatically show the location of that lesion in the center of the planar image displays and mark that location with the range markers 1513-1514 and an optional additional indicator.

According to another preferred embodiment for use in conjunction with each of the above embodiments is a reverse-locating capability from a first location of interest on a planar ultrasound image to a corresponding location on the proper corresponding thick-slice image. During review of the planar ultrasound images 1506 and 1508 as the user is moving the cursor 1512/1704 around the active thick-slice member image 1510, the user may see an interesting location appear somewhere on one of the planar ultrasound images 1506 or 1508. When this occurs, the user can right-click the mouse or press a "reverse locator" button (not shown) on keypad 1822. Responsive thereto, the cursor 1512/1704 transforms into a reverse locator pointer, such as by turning into a bright-yellow arrow. The user then moves this arrow over to the first location of interest in the planar ultrasound image 1506 or 1508 and then left-clicks or presses the "reverse locator" button again. Responsive to the selection of the first location of interest, (i) the yellow arrow disappears, (ii) the thick-slice image corresponding to the first location of interest becomes the active thick-slice member image, and (iii) the cursor 1512/1704 re-appears at a location corresponding to that first location of interest. The reverse-locating capability is usable regardless of whether the current display mode is of the thick-slice array 1502 or the enlarged thick-slice view 1702. In the event that the current display mode is the enlarged thick-slice view 1702, the currently-displayed thick-slice image is replaced, if necessary, by a different thick-slice image corresponding to the depth of the first location of interest.

An adjunctive ultrasound system according to the preferred embodiments does not supplant existing x-ray mammogram screening methods. Indeed, reference to the adjunctive ultrasound data is optional depending on the contents of the x-ray mammogram image, and for many patients it may not even be used at all. Rather, the adjunctive ultrasound system is there to assist the radiologist in performing their pre-existing professional duties with respect to "difficult" or "marginal" mammograms. As such, a medical establishment faces little risk of failure in acquiring an adjunctive ultrasound system according to the preferred embodiments. In a worst-case scenario, the adjunctive ultrasound system would be met with indifference by the entrenched "x-ray-only" believers, because it would not disturb their pre-existing routines. However, the adjunctive ultrasound system will be there standing by to assist in the "difficult" cases, and it is expected that even the "x-ray-only" believers will eventually find the system useful and will increasingly rely on it to increase their sensitivity and specificity performance.

Also within the scope of the preferred embodiments is a computer program product for instructing one or more processors to carry out one or more of the methods of the preferred embodiments, such computer program product being amenable to ready implementation by a person skilled in the art in view of the present disclosure. In one preferred embodiment, the computer program product is executed primarily by the ultrasound server 106 of FIG. 1, with the other system devices of FIG. 1 performing simple input/ output, display, and storage functions. In other preferred embodiments, the computer program product is distributed across the different systems of FIG. 1, with different algorithmic portions being carried out by different systems or subsystems. Ultrasound server 106 comprises a computer system that includes a cabinet, a display monitor, a keyboard, and a mouse, the mouse having one or more buttons for interacting with a graphical user interface. The cabinet typically houses a CD-ROM, zip, and/or floppy disc drive, system memory and a hard drive which can be utilized to store and retrieve software programs incorporating computer code that implements the preferred embodiments, data for use with the invention, and the like. An external hard drive is also shown in FIG. 1. Although CD-ROM, zip, and floppy discs represent common computer readable storage mediums, other computer readable storage media including tape, flash memory, system memory, and hard drives can be used. Additionally, a data signal embodied in a carrier wave, such as in a network including the Internet or an intranet, can form the computer readable storage medium.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although described supra in terms of adjunctive ultrasound screening, in view of the present disclosure one skilled in the art would readily be able to apply the thick-slice display apparatus of the preferred embodiments in the context of computerized tomography (CT) and/or magnetic resonance imaging (MRI) environments. In each case, individual image slices generated from CT scans or MRI scans of the breast are compounded so as to form thick-slice images of slab-like portions of the breast along planes parallel to a standardized x-ray mammogram view plane, and the thick-slice images are displayed to the radiologist in close proximity to an x-ray mammogram of the breast to assist in interpreting that x-ray mammogram. Preferably, a single composite view of the whole breast is shown together with the thick-slice image views, these views having their grayscale polarities toggled and/or remapped such that they are reminiscent of x-ray mammogram views taken from the standardized direction. By way of further example, the preferred embodiments described supra may also be used with different ultrasound modalities other than B-mode scans, including power or color Doppler modalities, and may also be used in conjunction with vibrational Doppler imaging (VDI) modalities. Therefore, reference to the details of the preferred embodiments are not intended to limit their scope, which is limited only by the scope of the claims set forth below.

What is claimed is:

1. A method for computing a two-dimensional thick-slice ultrasound image from a volumetric ultrasound representation of a breast, said volumetric ultrasound representation comprising ultrasonic property values for voxels of the breast, said thick-slice ultrasound image comprising values for pixels and corresponding to a first slab-like subvolume of the breast lying between a first border plane and a second border plane thereof, comprising:
    identifying for a first pixel location in the thick-slice ultrasound image a first voxel set corresponding to a voxel column in said volumetric ultrasound representation passing through the first pixel location and extending from the first border plane to the second border plane;
    identifying a thickness of the first slab-like volume between the first border plane and the second border plane;
    identifying a mass size of interest;
    identifying a target size to slab thickness ratio based on the identified thickness and mass size of interest;
    computing one or more statistical properties of said first voxel set;
    identifying a pixel value based on the one or more statistical properties of the first voxel set and the target size to slab thickness ratio; and
    setting an output value for the first pixel location to the identified pixel value.

2. The method of claim 1, further comprising computing a respective output value for each additional pixel location using one or more statistical properties of respective additional voxel sets, said one or more statistical properties incurring changes across different pixel locations in mass localities that are more significant for masses greater than the mass size of interest and that are less significant for masses smaller than said mass size of interest, mass lesions greater than said mass size of interest being emphasized and mass lesions smaller than said mass size of interest being de-emphasized in said thick-slice ultrasound image.

3. The method of claim 2, said identifying pixel value comprising:
    computing a histogram of values of said first voxel set;
    computing at least a portion of a cumulative distribution function from said histogram;
    determining a first pixel level for which said cumulative distribution function is equal to the target size to slab thickness ratio times a coefficient value; and
    setting said output value equal to said first pixel level, and wherein the method further comprises displaying the thick-slice ultrasound image with the output value for the first pixel location.

4. The method of claim 3, said coefficient value being a fixed value.

5. The method of claim 4, wherein the coefficient value is between 0.20 and 0.45.

6. The method of claim 3, said coefficient value being variable for different pixel locations in said thick-slice ultrasound image.

7. A method for computing a two-dimensional thick-slice ultrasound image from a volumetric ultrasound representation of a breast, said volumetric ultrasound representation comprising ultrasonic property values for voxels of the breast, said thick-slice ultrasound image comprising values for pixels and corresponding to a first slab-like subvolume of the breast lying between a first border plane and a second border plane thereof, the breast further having a second slab-like subvolume immediately adjacent to the first slab-like subvolume, the method comprising:
    identifying for each pixel location in the thick-slice ultrasound image a first voxel set corresponding to a voxel column in said volumetric ultrasound representation passing through that pixel location and extending from the first border plane to the second border plane;
    computing one or more statistical properties of said first voxel set;
    computing an output value for that pixel location using said one or more statistical properties of said first voxel set;
    identifying for each pixel location in the thick-slice ultrasound image a second voxel set corresponding to said voxel column extending from a first intermediate elevation in said first slab-like subvolume to a second intermediate location in said second slab-like subvolume, said first and second voxel sets having the same number of voxels;

computing one or more statistical properties of said second voxel set;

computing an alternative result for that pixel location using said one or more statistical properties of said second voxel set; and if said alternative result indicates an ultrasound echo intensity less than that indicated by said output value, resetting said output value to said alternative result.

8. The method of claim 7, said volumetric ultrasound representation being formed from scans taken during a sweep of an ultrasound probe across the breast, wherein said second slab-like subvolume is closer to a locus of said ultrasound probe sweep than said first slab-like subvolume.

9. The method of claim 1, further comprising:

identifying for a second pixel location in the thick-slice ultrasound image a second voxel set corresponding to a voxel column in said volumetric ultrasound representation passing through the second pixel location and extending from the first border plane to the second border plane;

computing one or more statistical properties of said second voxel set; and computing an output value for the second pixel location using said one or more statistical properties of said second voxel set, the target size to slab thickness ratio, and a coefficient value, and where the computed one or more statistical properties of the second voxel set are different than the computed one or more statistical properties of the first voxel set.

* * * * *